(12) United States Patent
Wormsbecher

(10) Patent No.: US 7,314,845 B2
(45) Date of Patent: Jan. 1, 2008

(54) SUPPORTED CATALYST SYSTEMS

(76) Inventor: Richard Franklin Wormsbecher, 13521 Orion Dr., Dayton, MD (US) 21036

(*) Notice: Subject to any disclaimer, the term of this patent is extended or adjusted under 35 U.S.C. 154(b) by 393 days.

(21) Appl. No.: 11/132,970

(22) Filed: May 19, 2005

(65) Prior Publication Data
US 2006/0000758 A1    Jan. 5, 2006

Related U.S. Application Data

(60) Division of application No. 10/357,115, filed on Feb. 3, 2003, now Pat. No. 6,987,079, which is a continuation-in-part of application No. 09/929,621, filed on Aug. 14, 2001, now Pat. No. 6,802,966.

(51) Int. Cl.
*B01J 31/00* (2006.01)
(52) U.S. Cl. .............. 502/172; 502/150; 502/439; 423/659; 210/198.2; 210/502.1; 210/656
(58) Field of Classification Search ........... 210/635, 210/656, 198.2, 502.1, 763; 423/659; 502/150, 502/172, 439
See application file for complete search history.

(56) References Cited

U.S. PATENT DOCUMENTS

| | | | |
|---|---|---|---|
| 3,666,530 A | 5/1972 | Aue | 428/429 |
| 3,669,841 A | 6/1972 | Miller | 195/63 |
| 3,715,278 A | 2/1973 | Miller | 195/63 |
| 3,795,313 A | 3/1974 | Kirkland et al. | 210/198.2 |
| 3,873,426 A | 3/1975 | Katchalski et al. | 195/63 |
| 3,954,678 A | 5/1976 | Marquisee | 252/451 |

(Continued)

FOREIGN PATENT DOCUMENTS

| | | |
|---|---|---|
| EP | 303406 | 2/1989 |
| EP | 0 425 104 | 2/1991 |
| GB | 1 283 958 | 8/1972 |
| WO | WO 87/06586 | 11/1987 |
| WO | WO 98/31461 | 7/1998 |
| WO | WO 03/015915 | 8/2001 |

OTHER PUBLICATIONS

Greg T. Hermanson, A. Krishna Mallia, and Paul K. Smith, "Immobilized Affinity Ligand Techniques", (Academic Press. Inc., San Diego, CA. 1992) (TOC).

(Continued)

*Primary Examiner*—Ernest G. Therkorn
(74) *Attorney, Agent, or Firm*—Charles A. Cross

(57) ABSTRACT

The present invention relates to a supported catalyst system. The supported catalyst of the present invention comprises an inorganic support having attached to at least one surface thereof non-acidic, hydrophilic, hydroxyl-containing organic $R_{10}$ groups having no or substantially no surface charge in solution, and at least one linker capable of binding a catalytic species, e.g. an enzyme or an organometallic molecule, wherein the linker is attached to a catalytic species. The $R_{10}$ groups preferably are selected from the group consisting of —$CH_2OH$, —$CH(OH)_2$, —$CH(OH)CH_3$, —$CH_2CH_2OH$, —$CH(OH)_2CH_3$, —$CH_2CH(OH)_2$, —$CH(OH)CH_2(OH)$ and mixtures thereof. The presence of the $R_{10}$ groups on the support surface prevents or reduces non-specific binding of the catalytic species with the support surface by minimizing hydrophobic interactions and providing no or substantially no surface charge in the region of the support having catalytic species attached thereto. Simultaneously, the linker binds the catalytic species to the surface of the support in a manner which permits the catalytic species to be freely available for catalytic activity. Methods of catalyzing a reaction using the supported catalyst system of the invention are also disclosed.

25 Claims, 23 Drawing Sheets

U.S. PATENT DOCUMENTS

| | | | |
|---|---|---|---|
| 3,983,000 A | 9/1976 | Messing et al. | 195/63 |
| 3,983,299 A | 9/1976 | Regnier | 428/405 |
| 4,034,139 A | 7/1977 | Mazarguil et al. | 428/405 |
| 4,043,905 A | 8/1977 | Novotny et al. | 210/31 C |
| 4,177,038 A | 12/1979 | Biebricher et al. | 8/192 |
| 4,206,259 A | 6/1980 | Rohrbach et al. | 428/304 |
| 4,258,133 A | 3/1981 | Mirabel et al. | 435/176 |
| 4,268,423 A | 5/1981 | Rohrbach et al. | 252/430 |
| 4,298,500 A | 11/1981 | Abbott | 252/428 |
| 4,384,045 A | 5/1983 | Ho et al. | 435/176 |
| 4,415,663 A | 11/1983 | Symon et al. | 435/176 |
| 4,425,434 A | 1/1984 | Rosevear | 435/176 |
| 4,430,496 A | 2/1984 | Abbott | 536/27 |
| 4,469,630 A | 9/1984 | Flashner | 260/112 B |
| 4,520,122 A | 5/1985 | Arena | 502/152 |
| 4,540,486 A | 9/1985 | Ramsden | 210/198.2 |
| 4,544,485 A | 10/1985 | Pinkerton et al. | 210/502 |
| 4,551,245 A | 11/1985 | Ramsden et al. | 210/198.2 |
| 4,606,825 A | 8/1986 | Crane et al. | 210/635 |
| 4,681,870 A | 7/1987 | Balint, Jr. et al. | 502/403 |
| 4,742,159 A | 5/1988 | Batz et al. | 530/388 |
| 4,778,600 A | 10/1988 | Williams | 210/198.2 |
| 4,828,695 A | 5/1989 | Yamamura et al. | 210/198.2 |
| 4,837,348 A | 6/1989 | Stolowitz et al. | 556/9 |
| 4,918,016 A | 4/1990 | Leuba et al. | 435/176 |
| 4,925,818 A | 5/1990 | Schneider et al. | 502/7 |
| 4,994,429 A | 2/1991 | Wieserman et al. | 502/401 |
| 5,002,884 A | 3/1991 | Kobayashi et al. | 435/176 |
| 5,035,803 A | 7/1991 | Cohen | 210/656 |
| 5,043,062 A | 8/1991 | Bale et al. | 210/198.2 |
| 5,045,190 A | 9/1991 | Carbonell et al. | 210/198.2 |
| 5,055,194 A | 10/1991 | Goetz et al. | 210/635 |
| 5,075,423 A | 12/1991 | Balint, Jr. | 530/350 |
| 5,077,210 A | 12/1991 | Eigler et al. | 435/176 |
| 5,085,779 A | 2/1992 | Crane et al. | 210/635 |
| 5,118,796 A | 6/1992 | Prior et al. | 530/388.1 |
| 5,137,627 A | 8/1992 | Feibush | 210/198.2 |
| 5,167,812 A | 12/1992 | Graves et al. | 210/198.2 |
| 5,240,602 A | 8/1993 | Hammen | 210/198.2 |
| 5,277,813 A | 1/1994 | Feibush et al. | 210/502.1 |
| 5,362,859 A | 11/1994 | Zale | 530/413 |
| 5,371,262 A | 12/1994 | Arkles | 556/449 |
| 5,374,755 A | 12/1994 | Neue et al. | 556/400 |
| 5,403,750 A | 4/1995 | Braatz et al. | 436/531 |
| 5,405,766 A | 4/1995 | Kallury et al. | 435/174 |
| 5,431,807 A | 7/1995 | Frechet et al. | 210/198.2 |
| 5,527,711 A | 6/1996 | Tom-Moy et al. | 436/518 |
| 5,605,793 A | 2/1997 | Stemmer | 435/6 |
| 5,652,348 A | 7/1997 | Burton et al. | 536/20 |
| 5,663,051 A | 9/1997 | Vlasselaer | 435/7.23 |
| 5,667,692 A | 9/1997 | Muller | 210/635 |
| 5,744,302 A | 4/1998 | Sessler et al. | 435/6 |
| 5,811,238 A | 9/1998 | Stemmer et al. | 435/6 |
| 5,821,193 A | 10/1998 | Tani et al. | 502/401 |
| 5,830,721 A | 11/1998 | Stemmer et al. | 435/172.1 |
| 5,945,520 A | 8/1999 | Burton et al. | 536/20 |
| 5,948,428 A | 9/1999 | Lee et al. | 424/426 |
| 5,965,408 A | 10/1999 | Short | 435/91.1 |
| 5,993,653 A | 11/1999 | Ahmed et al. | 210/198.2 |
| 5,998,183 A | 12/1999 | Le Fevre et al. | 435/176 |
| 6,013,855 A | 1/2000 | McPherson et al. | 623/11 |
| 6,025,129 A | 2/2000 | Nova et al. | 435/6 |
| 6,045,697 A | 4/2000 | Girot et al. | 210/635 |
| 6,117,679 A | 9/2000 | Stemmer | 435/440 |
| 6,132,970 A | 10/2000 | Stemmer | 435/6 |
| 6,165,793 A | 12/2000 | Stemmer | 435/440 |
| 6,180,406 B1 | 1/2001 | Stemmer | 435/440 |
| 6,238,884 B1 | 5/2001 | Short et al. | 435/69.1 |
| 6,251,278 B1 | 6/2001 | Hammen | 210/635 |
| 6,447,911 B1 | 9/2002 | Pryor et al. | 428/404 |
| 6,802,966 B2 | 10/2004 | Wormsbecher | 210/198.2 |
| 6,987,079 B2 * | 1/2006 | Wormsbecher | 502/172 |
| 6,998,042 B2 * | 2/2006 | Wormsbecher | 210/198.2 |
| 7,166,213 B2 * | 1/2007 | Wormsbecher | 210/198.2 |
| 2002/0034613 A1 | 3/2002 | Liu et al. | 428/195 |
| 2003/0082658 A1 | 5/2003 | Mallet et al. | 435/7.92 |

OTHER PUBLICATIONS

Affinity Separations, A Practical Approach, Ed. Paul Matejtschuk; pp. 1-38, undated.

ASTM D 5373-93 (Reapproved 1997)—"Standard Test Methods for Instrumental Determination of Carbon, Hydrogn, and Nitrogen in Laboratory Samples of Coal and Coke"; pp. 1-4, undated.

ASTM D 5291-96; "Standard Test Methods for Instrumental Determination of Carbon, Hydrogen, and Nitrogen in Petroleum Products and Lubricants"; pp. 852-856, undated.

Legrand, Andre P, "The Surface Properties of Silica," John Wiley & Sons, 1998, Chap. 3 & 4.

Chapman, Robert C. et al., J. Am. Chem. Soc 2000, 122, 8303-8304—"Surveying for Surfaces that Resist the Adsorption of Proteins".

Sie, S.T., "Intraparticle Diffusion & Reaction Kinetic Gas Factors in Catalyst Particle Design"; The Chemical Engineering Journal, vol. 53, (1993), pp 1-11.

Smith, "Organic Synthesis" (John Wiley & Sons, 1994.) (TOC).

March, "Advanced Organic Chemistry" (4th Ed.) (John Wiley & Sons, 1992) (TOC).

Cornils et al., "Applied Homogeneous Catalysis with Organometallic Compounds" (vol. 3) (Wiley—VHC, 2002) (TOC).

De Vos, D.E., et al., "Chiral Catalyst Immobilization and Recycling" (Wiley—VC, 2002); (TOC).

Larock, "Comprehensive Organic Transformation" (2nd Ed.) (J. Wiley & Sons, 1999) (TOC).

Green et al., "Protective Groups in Organic Synthesis" (3rd Ed.) (J. Wiley & Sons, 1999) (TOC).

Brook, "Silicon In Organic, Organometallic, and Polymer Chemistry" (J. Wiley and Sons, 2000); (TOC).

Weetall, "Covalent Coupling Methods for Inorganic Support Materials", in Methods in Enzymology, vol. XLIV, ed. Mosbach, K. (1976); (TOC).

Sindorf, D.W. et al., J. Am. Chem. Soc., 105:3767-3776 (1983).

Moulder, J.F. et al., "Handbook of X-ray Photoelectron Spectroscopy", Perkin-Elmer Corp., Eden Prairie, MN (1992); (TOC).

Snyder, Introduction to Modern Liquid Chromatography, John Wiley, 1979, p. 789.

* cited by examiner

Specific Activity

Lipase Transesterification Reaction Rates

FIG. 17
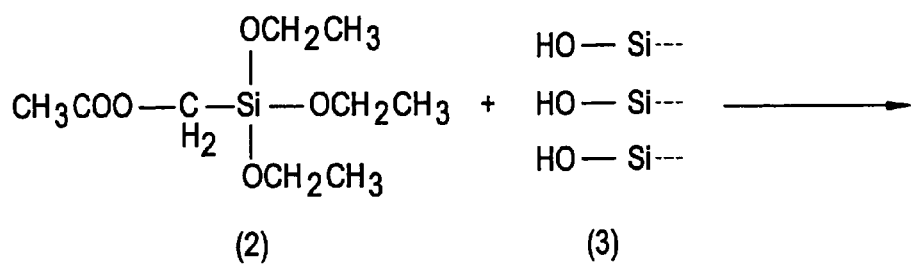
(2)                (3)
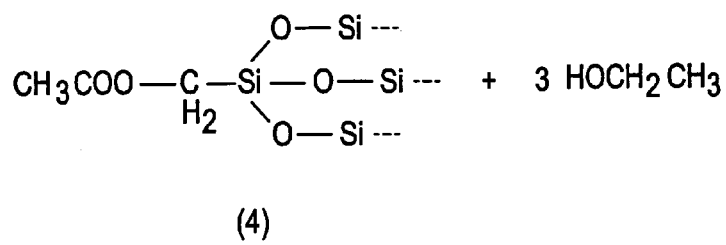
(4)
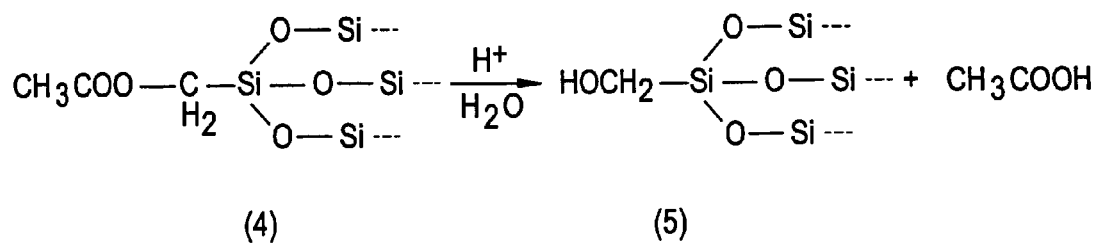
(4)                (5)

FIG. 18
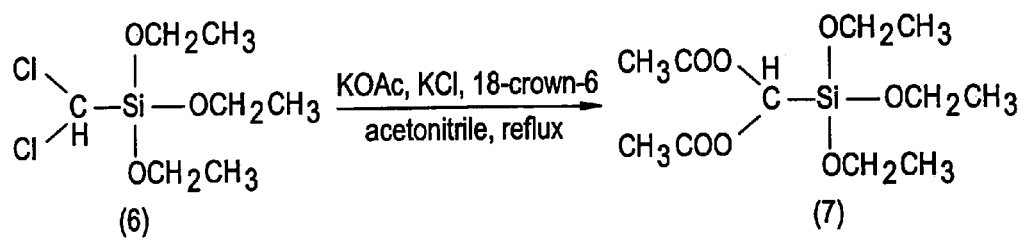
FIG. 19
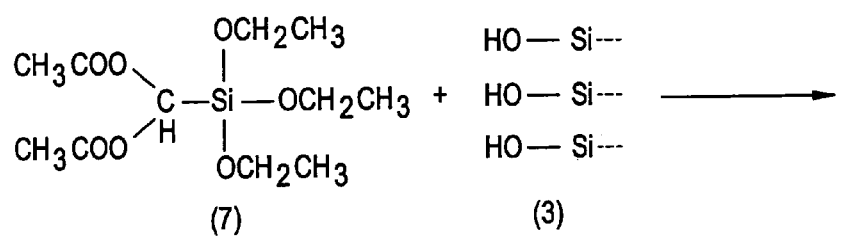
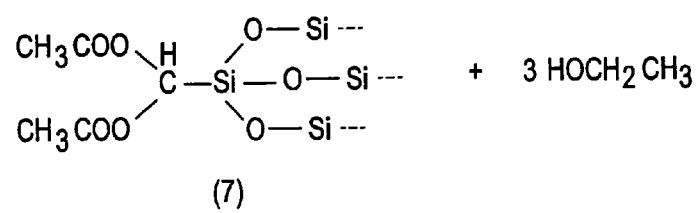
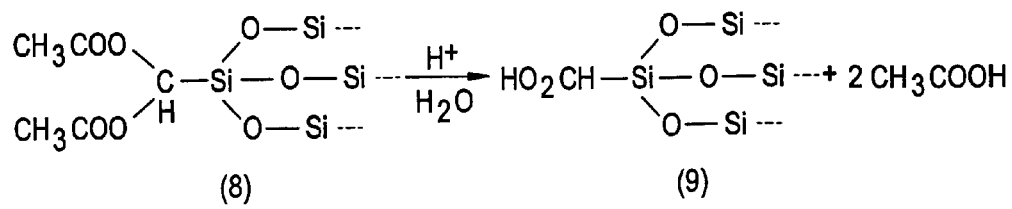

(15)

FIG. 25
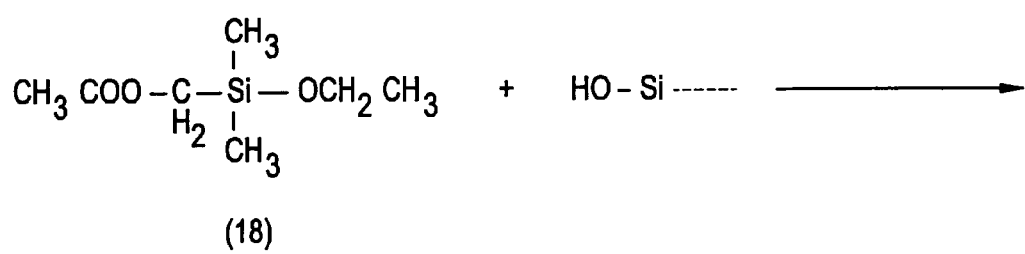
(18)
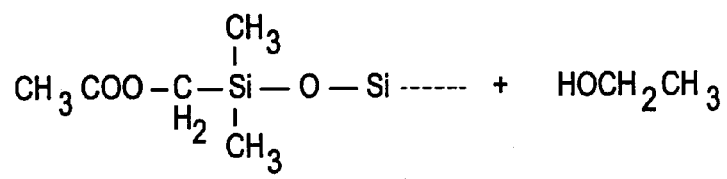
(19)
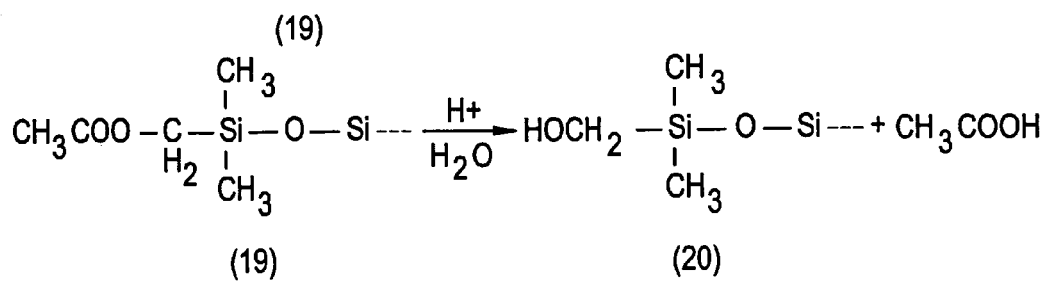
(19)  (20)

SUPPORTED CATALYST SYSTEMS

RELATED APPLICATIONS

This application is a division of U.S. Ser. No. 10/357,115, filed Feb. 3, 2003, now U.S. Pat. No. 6,987,079, which, in turn is a continuation-in-part of U.S. application Ser. No. 09/929,621 filed Aug. 14, 2001, now U.S. Pat. No. 6.802, 966 the contents of which are incorporated by reference herein.

FIELD OF THE INVENTION

The present invention is directed to novel catalyst systems, and the use thereof in catalysis. More specifically, the present invention relates to supported catalyst systems having at least one catalytic species, e.g. an enzyme or organometallic complexes, immobilized or attached on at least one surface of a support, which surface has been modified to prevent non-specific binding of the catalytic species to the support. The catalyst systems exhibit high catalytic activity and permits easy separation and recovery of the catalytic species for reuse.

BACKGROUND OF THE INVENTION

The synthesis of fine chemicals and pharmaceuticals has become increasingly more complicated often requiring multi-step reactions involving complicated catalyst systems, such as, e.g., expensive enzyme and organometallic-based catalyst systems. Consequently, there has been increased emphasis on the development of new and improved catalyst systems which have high activity and selectivity, are easily recovered from reaction solutions for subsequent reuse and will maintain their catalytic activity for a relatively extended period of time under desired reaction conditions.

One such catalyst system which has shown great industrial potential in the field of biocatalysis, for example, are based on enzymes. Enzymes are proteinaceous catalytic materials that often exhibit the advantages of catalyzing difficult or complexed reactions with great chemical specificity under relatively mild conditions. For these reasons, there is increased emphasis on the use of enzyme-based catalysts in the food and pharmaceutical industries on a commercial scale.

Enzymes are generally soluble making recovery of the enzyme for reuse difficult, if not impossible. In some cases, the processing conditions may destroy the enzyme. Where the enzyme is not destroyed, it may be necessary to destroy it, as in the case of some food products, where continued activity would have an unwanted effect. To avoid these problems, fixed or immobilized enzyme systems have been developed where the enzyme is bonded onto the surface of an inorganic support or carrier. Exemplary immobilized enzyme systems, and the methods for the preparation thereof, are disclosed in U.S. Pat. Nos. 4,384,045; 4,258, 133; 5,998,183; and 5,405,766.

Other catalysts of interest include organometallic complexes, which are widely used in the synthesis of fine chemicals and pharmaceuticals. Organometallic complexes catalyze many important reactions, such as, for example, Heck-type reactions, Suzuki coupling reactions, animation of aromatic halides, and Grignard reactions. In most applications, organometallic complex catalysis is performed in the homogeneous mode, where separation and reuse of the catalyst is difficult. Often, organometallic complexes are very expensive, so that reuse and recovery is highly desirable. A considerable amount of research has been aimed at "heterogenizing" the homogeneous organometallic complex catalysts, so that recovery of the catalysts is simplified. See, e.g., Cornils et al., *Applied Homogenous Catalysis with Organometallic Compounds* (Volume 3) (Wiley-VHC, 2002); and D. E. DeVos et al., *Chiral Catalyst Immobilization and Recycling* (Wiley-VC, 2002).

It is well known that many catalytic species, e.g., proteins, bind very strongly, and sometimes irreversibly and non-selectively, to certain support materials, in particularly, inorganic oxide-based materials. Further, where the inorganic oxide support contains a functionality such as hydroxyl groups, in particularly, acidic hydroxyl groups, the support can suffer an even higher degree of non-selective binding of the catalytic species. That is, the catalytic species, e.g., an enzyme, can bind to the surface of a support in a non-selective fashion decreasing catalytic activity. Therefore, while catalytic functionality on the surface can be very selective for the desired catalysis, the unused regions of the surface are often non-selective. The net effect is to lower the activity of the catalyst composite.

Consequently, there exists a need for improved supported catalyst systems which prevents or minimizes problems of non-specific binding associated with known supported catalyst systems, allow for easy recovery of the catalyst system from reaction solutions for subsequent reuse and maintain high catalytic activity for an extended period of time.

SUMMARY OF THE INVENTION

Novel supported catalyst systems have now been developed which prevent or reduce nonspecific binding to the support comprising the catalyst systems, in particular, an inorganic oxide support having acidic hydroxyl groups on at least one surface thereof. Development of the catalyst systems of the invention is based on the discovery that modification of the support surface to minimize surface hydrophobic interactions and provide a zero or low surface charge in the region of the support having catalytic species attached thereto, minimizes or reduces non-specific binding to the support.

In accordance the present invention, the supported catalyst systems comprise a catalytic species, e.g., an enzyme or other catalytic species, immobilized or bound to at least one surface of a support by means of at least one linker attached to the at least one surface of the support in a region wherein the support surface has been modified to provide a plurality of $R_{10}$ groups. Preferably, the $R_{10}$ groups are selected from the group consisting of: $-CH_2OH$, $-CH(OH)_2$, $-CH(OH)CH_3$, $-CH_2CH_2OH$, $-CH(OH)_2CH_3$, $-CH_2CH(OH)_2$, $-CH(OH)CH_2(OH)$ and mixtures thereof. The presence of the $R_{10}$ groups on the support surface prevents or reduces all or substantially all surface interactions, especially reactions from more polar solvents, such as water, while the linker binds the catalytic species to the surface of the support in a manner which permits the catalytic species to be freely available for catalytic activity.

Supported catalyst systems in accordance with the invention exhibit high catalytic activity for an extended period of time under desired reaction conditions and provide ease of recovery of the catalytic species from reaction for reuse.

Without being bound to any particular theory, it is believed that, to avoid non-selective binding to a support surface, the surface charge of the support should be zero or very low. Moreover, avoiding a surface charge reduces or prevents the strong attractive electrostatic forces, which can denature certain catalytic species, such as enzymes or organometallic complexes, leaving them catalytically inactive. In addition to avoiding a surface charge, surface hydrophobic interactions should be minimized or eliminated to reduce non-selective binding. Hydrophobic interactions, generally weaker than electrostatic or dipole interactions can become dominant when the salt concentration of the solvent of a protein mixture, such as an enzyme-containing mixture, is relatively high. The ions of the salt interact with the charged surface of the support, thereby "screening the charge" from the proteins via the electrical double layer. The resultant high salt concentration allows hydrophobic interactions to become more dominant. Such a hydrophobic support surface should be avoided to minimize or eliminate hydrophobic interactions.

Dipole interactions, e.g., hydrogen bonding, are also believed to play a role in non-selective binding and thus, should be taken into consideration. For example, if the solvent is water, then the dipole interactions favor the solvent over the support surface due to entropy considerations. More specifically, binding a component from a solution to a support surface involves a lowering of entropy due to the localization of the component on the surface. That is, if a protein, such as an enzyme, has a "choice" of binding to a surface through hydrogen bonding or remaining in solution, the latter is favored because of its higher entropy state.

For adsorption from solution to occur at all, the interaction energy of an adsorbing molecule with a surface, the enthalpy of adsorption, must overcome higher entropy of solution. Adsorption or non-selective binding to a surface always represents a lowering of entropy from a solution. For this lowering to occur, the enthalpy of adsorption must be high enough to overcome the entropy change. That is, both electrostatic and hydrophobic interactions should be avoided, namely to keep the enthalpy of adsorption low.

Accordingly, it is an advantage of the present invention to provide improved supported catalyst systems wherein the support has a reduced ability to non-specifically bind to unwanted non-catalytic materials.

Another advantage of the present invention is to provide supported catalyst systems wherein the support has no or substantially no surface charge at the operating pH of adsorption and is hydrophilic in nature.

It is yet another advantage of the present invention to provide supported catalyst systems wherein the support has a reduced ability for hydrophobic interactions.

Another advantage of the present invention is to provide supported catalyst systems wherein the support has a reduced ability for electrostatic interactions.

Another advantage of the present invention is to provide supported catalyst systems wherein the support has a reduced ability for both electrostatic and hydrophobic interactions, thereby maintaining a low enthalpy of adsorption.

Another advantage of the present invention is to provide inorganic oxide supported catalyst systems, which resists nonspecific binding.

Yet another advantage of the present invention is to provide improved enzyme-based supported catalyst systems, which exhibit high enzymatic activity and allow for ease of catalyst recovery for reuse.

It is also an advantage of the present invention to provide improved organometallic-based supported catalyst systems, which exhibit high catalytic activity and allow for ease of catalyst recovery for reuse.

It is also an advantage of the present invention to provide methods of reducing or preventing unwanted non-specific binding of non-catalytic species to a support comprised in a supported catalyst system.

These and other aspects of the present inventory are described in further detail below.

BRIEF DESCRIPTION OF THE DRAWINGS

FIG. 17 shows the preparation of silica having $R_{10}$ attached via a silicon atom which is not a part of the silica, in which $R_{10}$ is —$CH_2OH$, so that —Si—$CH_2OH$ is directly attached to the surface (SiOH represents a silanol group on the surface).

FIG. 18 depicts the preparation of a coating agent that yields —$CH(OH)_2$ as $R_{10}$, from the reaction illustrated in FIG. 19.

FIG. 19 shows the preparation of silica having $R_{10}$ indirectly attached via a silicon atom which is not a part of the silica, in which $R_{10}$ is —$CH(OH)_2$, so that —Si—CH$(OH)_2$ is directly attached to the surface (SiOH represents a silanol group on the surface).

FIG. 25 shows an embodiment of the present invention in which the —Si—$R_{10}$ group is attached to a silica surface at a single point. $R_{10}$ is hydroxymethyl (SiOH represents a silanol group on the surface).

DETAILED DESCRIPTION OF THE INVENTION

Figure 1:
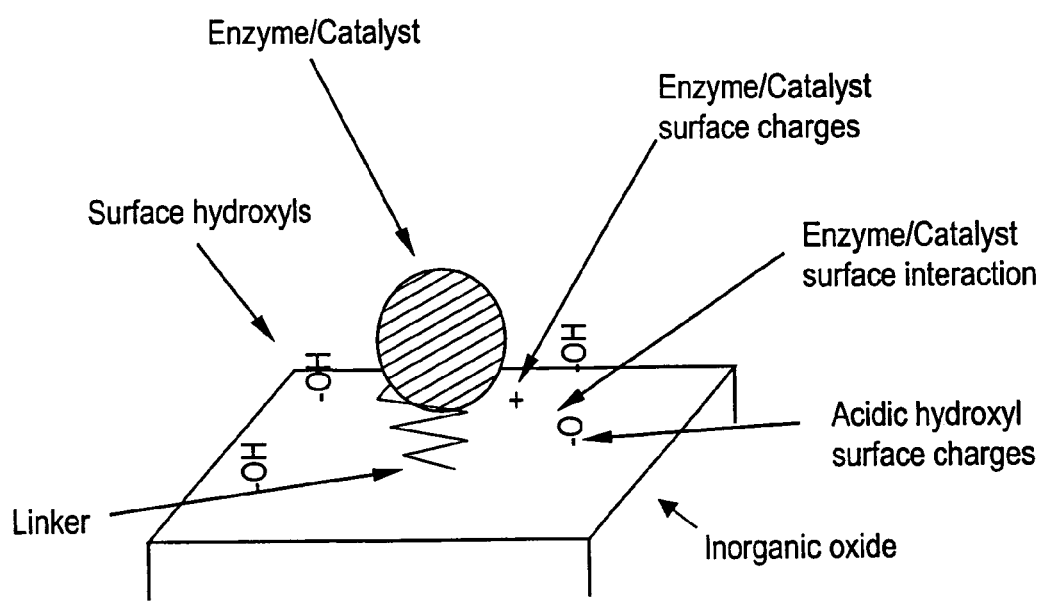
FIG. 1 schematically depicts an immobilized enzyme system where an enzyme is attached via a linker to the surface of an inorganic oxide support, such as silica, without the inventive catalyst surface modification.

Throughout the application, the following definitions apply:

The phrase "catalytic species" is used herein to indicate any molecule or molecule fragment capable of affecting the rate of a chemical reaction without itself being consumed or undergoing a chemical change.

The term "substrate" is used herein to refer to the reactant molecules participating in a catalytic reaction.

The terms "product" or "products" are used herein to refer to a molecule or molecules produced by the reaction of reactant molecules during the catalytic reaction.

The term "linker" as used herein is intended to encompass at least one linker, also known in the art as ligand, spacer, spacer arm, pendant, or leash. It is also within the scope of the present invention to use a mixture of linkers. In the case where multiple linkers are employed that possess different binding affinities, the use of more than one type of linker is contemplated to bind more than one type of catalytic species simultaneously or separately.

The phrase "$R_{10}$ group" (also referred to as "$R_{10}$ moiety"), more specifically defined below, is intended to cover at least one $R_{10}$ group. The use of mixtures of $R_{10}$ groups is encompassed by the invention.

The term "surface" refers to a single surface or multiple surfaces of the support.

The phrase "supported catalyst system" refers to the total composite of the modified support with $R_{10}$ groups and linker, and the catalytic species attached to the support via a linker.

The phrase "non-specific binding" is used herein to indicate the undesired surface adsorption of substrate, product, catalytic species, or other entity or molecule in a manner which reduces or degrades catalytic activity.

The term "hydrophilic" is used herein to refer to the property of having an affinity for water and polar molecules.

In accordance with the present invention, the supported catalyst systems comprise a support, preferably an inorganic substance-based support, modified by having bonded on a least one surface both, at least one $R_{10}$ group, and at least one linker. Preferably, the $R_{10}$ group is selected from the group consisting of: —$CH_2OH$, —$CH(OH)_2$, —CH(OH)$CH_3$, —$CH_2CH_2OH$, —$CH(OH)_2CH_3$, —$CH_2CH(OH)_2$, —CH(OH)$CH_2$(OH) and mixtures thereof. The linker attaches at least one catalytic species, e.g. an enzyme or other catalytic species, to the support surface. Thus, the support surface is modified to contain within a same region both $R_{10}$ groups which completely prevent the catalytic species, substrate, or product from interacting non-selectively with the support surface and at least one linker which selectively binds the desired catalytic species. In this way, the catalytic species is attached to the surface of the support via the linker thereby providing the known advantages of immobilized catalysts, and, at the same time, remaining free and unconstrained allowing for very little loss of activity. The modified support can be provided "as is" (without the catalytic species attached thereto) to a user of the supported catalyst system and the user can then react a desired catalytic species, e.g. an enzyme, an organometallic complex, or other catalytic species, with the linker. The linkers may optionally be capped or otherwise provided in a precursor form, which would require further chemical manipulation before reaction with the catalytic species.

Components of the Supported Catalyst System

Figure 2:
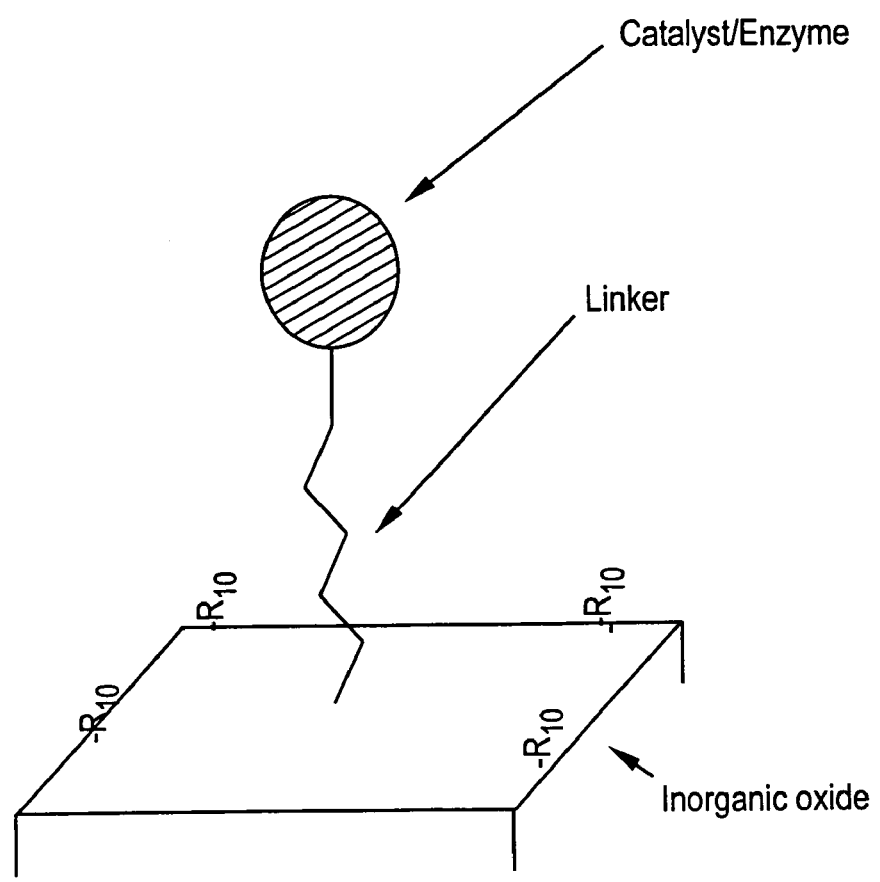
FIG. 2 schematically depicts an embodiment of the inventive supported catalyst system comprising an inorganic support, $R_{10}$ groups, a linker, and a catalytic species, i.e. an enzyme.

As discussed hereinabove, supported catalyst systems of the invention comprise a support, preferably an inorganic substance base support, most preferably an inorganic oxide support, having located on at least one surface of the support, at least one R10 group (defined below) and at least one linker, wherein the linker is capable of attaching to or is attached to a catalytic species, such as an enzyme. See, e.g., FIG. 2.

Inorganic Support

The preferred support material is an inorganic material that possesses a high surface area thereby providing a high capacity for binding catalytic species. It is also preferred that the inorganic material is physically robust to handle high-pressure loadings and is capable of handling high flow rates and high pressure.

Inorganic materials that can have high surface areas include, but are not limited to, silica gels, silicas, aluminas, and zirconias. In the case of silica gels, surface areas can range from very low, e.g., about 1 $m^2/g$, to very high, e.g., in excess of about 800 m²/g, with pore size modes from very low, e.g., less than about 25 Å, to very high, e.g., in excess of about 1500 Å. In addition, silicas not only possess a high surface area, but they are also physically robust, compared to polymeric materials, and can therefore be used in high pressure or high agitation conditions.

The preferred inorganic substance are inorganic oxides. Suitable inorganic oxides include, but are not limited to, those having about 1 to about 10 hydroxyl groups nm² of inorganic oxide. More preferably, the inorganic oxide is a metal oxide, silicate or aluminosilicate such as zeolite. The most preferred inorganic substance is an inorganic metal oxide such as silica and sodium silica, which may be in the form of, for example, chromatographic grade silica or silica gel. Additional preferred metal oxides include, but are not limited to, alumina, silica-alumina, zirconia, zirconate, controlled pore glass and titania. Magnetically responsive inorganic metal oxides, such as siliceous oxide-coated magnetic particles as disclosed in U.S. Pat. No. 6,447,911 (the entire disclosure of which is incorporated herein by reference) are also suitable as substrate materials. Mixed inorganic metal oxides, e.g., co-gels of silica and alumina or co-precipitates, can also be used.

The support may be in any form suitable to match the shape and/or size of reactor conditions, and thus, the support may be in any physical form such as particulates, fibers, or plates, prepared using methods known in the art. (See Sie, S. T., *The Chemical Engineering Journal*, Vol. 53(1993)). For example, spheres can be made for batch reactors and easy filtration and recovery, and extrudates can be made for continuous packed column applications. Silicas can be formed into many different shapes that can be used for different applications.

$R_{10}$ Groups $R_{10}$ groups useful to modify the support to provide the distinctive characteristic of reducing or preventing non-specific binding of a catalytic species directly to the support surface, include organic groups or moieties which are non-acidic, as compared to any hydroxyl groups on the support, hydroxyl containing groups which substantially do not possess a charge in solution. Organic groups suitable as $R_{10}$ groups have the common properties of being hydrophilic and non-acidic or very weakly acidic, i.e. having a $pK_a$ value of about 14 and greater. Preferably, the organic groups contain from about 1 to about 3 carbon atoms. When a reaction mixture having reactant molecules capable of forming a desired product is contacted with a support and the support has at least one $R_{10}$ group modified surface, charge interactions and hydrophobic interactions are minimized and dipole interactions are increased.

In a preferred embodiment of the invention, the $R_{10}$ group is an entity selected from the group consisting of —$CH_2OH$, —$CH(OH)_2$, —$CH(OH)CH_3$, —$CH_2CH_2OH$, —$C(OH)_2CH_3$, —$CH_2CH(OH)_2$, —$CH(OH)CH_2(OH)$ and mixtures thereof, and, particularly, —$CH_2OH$. More preferably, $R_{10}$ is selected from the group consisting of —$CH_2OH$, —$CH(OH)CH_3$, —$CH_2CH_2OH$ and —$CH(OH)CH_2(OH)$. Even more preferably, $R_{10}$ is selected from the group consisting of: —$CH_2OH$, —$CH(OH)CH_3$ and —$CH_2CH_2OH$. Most preferably, $R_{10}$ is —$CH_2OH$.

The moiety $R_{10}$ is located on at least one surface of the support. By "located" it is meant that $R_{10}$ can be attached directly to the surface of the support substance.

$R_{10}$ can be located on surface area present on the periphery of the inorganic support or located on surface area presented in pores, which penetrate into the interior of the support.

$R_{10}$ can also be "located" on the surface of the support by attachment to at least one support surface via a bivalent moiety or an atom (—X—) to form a group having the formula —X—$R_{10}$. The bivalent moiety or atom can be from a reactant employed to create $R_{10}$, e.g., a residual metal atom, such as silicon, originating from a silane reactant, aluminum from an aluminum alkoxide, or zirconium from a zirconium alkoxide. The bivalent moiety or atom may be attached directly to the support, preferably, through hydroxyl groups on the surface of the support. The support material selected may determine the selection of —X— and its associated reactant. However, generally, any reactant containing —X— will be that which can react with reactive functionalities, e.g., hydroxyl groups, on the support. In the case of inorganic oxides, suitable reactants typically include oxides capable of reacting with hydroxyl groups. For example, a support comprising $R_{10}$ groups located on at least one surface can be prepared using a reactant bearing the $R_{10}$ group, such as, for example, alkoxysilane, dialkoxysilane or trialkoxysilane. For instance, acetoxymethyl is the precursor group of the $R_{10}$ group hydroxymethyl. The method of attaching the $R_{10}$ group to the at least one support surface using a coating agent or reactant comprises first allowing the coating agent to react with the surface of the support, and then, hydrolyzing the precursor group within the coating agent to produce a support having $R_{10}$ groups attached. The chemistry of reacting compounds, e.g., those capable of creating $R_{10}$ groups, by reaction with inorganic substances is well known in the art. See, e.g., Smith, *Organic Synthesis* (John Wiley & Sons, 1994); March, *Advanced Organic Chemistry* ($4^{th}$ Ed.) (John Wiley & Sons, 1992); Larock, *Comprehensive Organic Transformations* ($2^{nd}$ Ed.) (John Wiley & Sons, 1999); Greene et al., *Protective Groups in Organic Synthesis* ($3^{rd}$ Ed.) (John Wiley & Sons, 1999); Brook, *Silicon in Organic, Organometallic, and Polymer Chemistry* (John Wiley & Sons, 2000); Hermanson, G. T. et al., *Immobilized Affinity Ligand Techniques* (Academic Press, Inc., San Diego, Calif., 1992); Weetall, *Covalent Coupling Methods for Inorganic Support Materials*, in *Methods in Enzymology*, vol. XLIV, ed. Mosbach, K. (1976); U.S. Pat. Nos. 4,298,500; and 5,371,262; the disclosures of which are incorporated by reference herein.

It is also within the scope of the present invention to have the $R_{10}$ groups attached to at least one surface of the support via a residual metal, e.g., Si, from a silane reactant wherein each resulting Si—$R_{10}$ group is attached to the support via three covalent bonds. See, for example, the final products of the reaction schemes in FIGS. 17, 19, 21 and 22, resulting from the reaction of a coating agent having three silanol groups.

Figure 23:
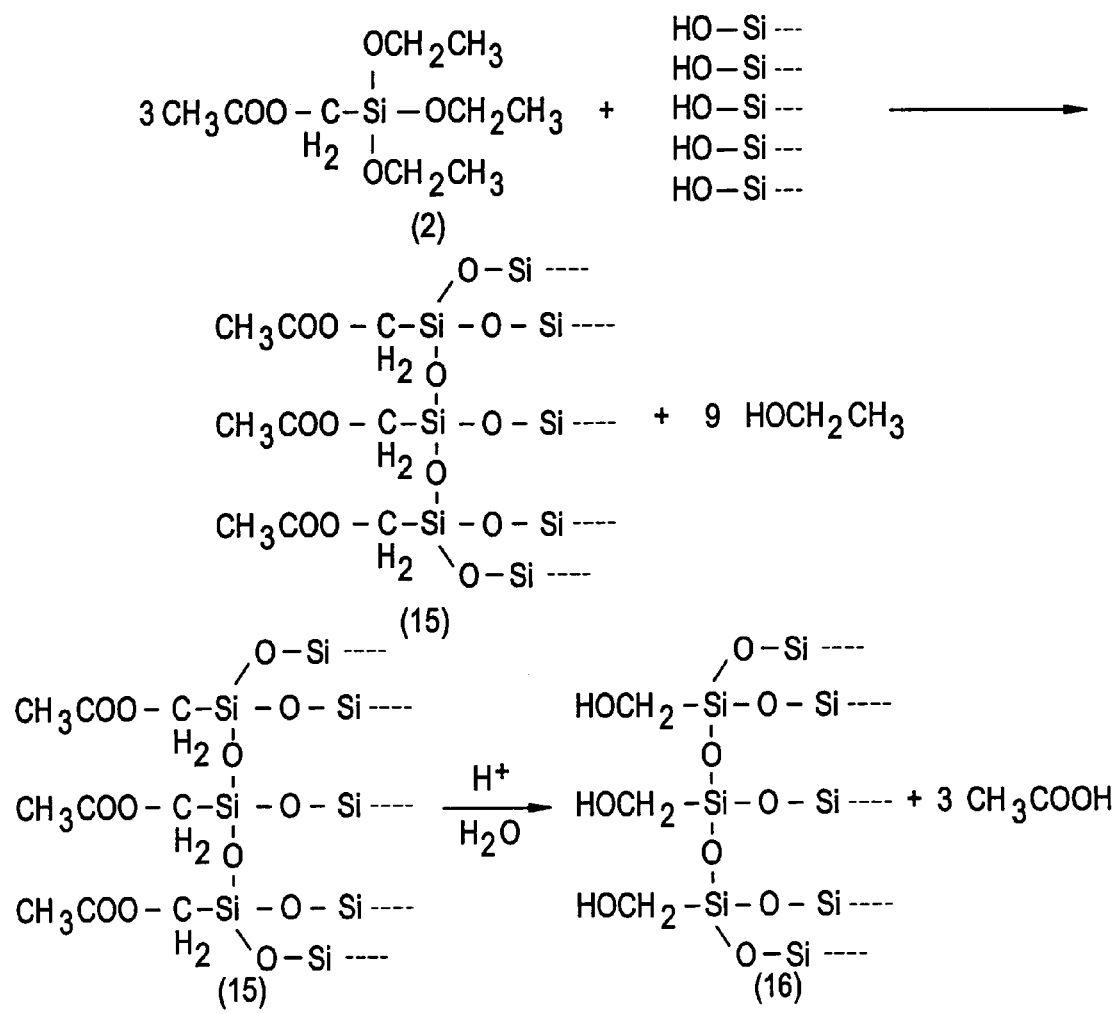
FIG. 23 shows an embodiment of the present invention in which —Si—$R_{10}$ groups are cross-linked when attached to a silica surface. $R_{10}$ is hydroxymethyl (SiOH represents a silanol group on the surface).
Figure 24:
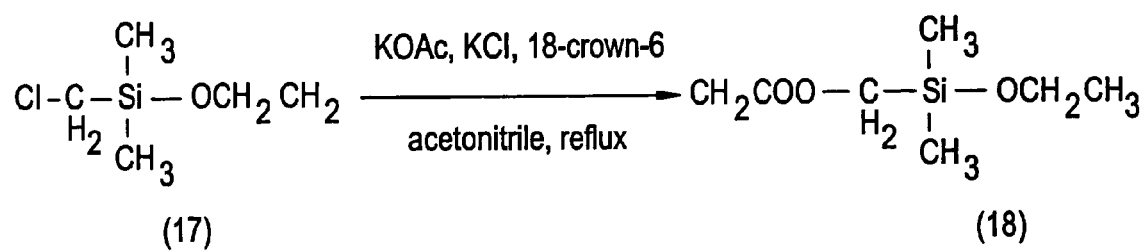
FIG. 24 shows the preparation of a coating agent that yields —Si—$R_{10}$ groups attached to a silica surface at a single point. $R_{10}$ is hydroxymethyl, resulting from the reaction illustrated in FIG. 25.

As illustrated in FIGS. 23 through 25, coating agents can be selected so that $R_{10}$ groups can be attached to the support substance via one or two covalent bonds, or via cross-linking of Si atoms. Such cross-linking can be a Si—O—Si linkage or another linkage such as Si—O—C(O)—O—Si, Si—O-alkylene-O—Si or Si—O—C(O)-alkylene-O—Si. The final product of the reaction scheme in FIG. 25, i.e., Compound (20), illustrates an embodiment of the inventive catalyst system wherein Si—$R_{10}$ groups have a single point of attachment to the surface of the silica. That embodiment is prepared from a reaction of silica and monoethoxysilane. See FIG. 24 for the preparation of the coating agent which is a monoethoxysilane.

Linkers

A linker is a low molecular weight molecule bound to both the support and the catalytic species and which acts as an immobilizing group for binding the catalytic species to the support. Thus, selection of an appropriate linker will depend upon the support material and the catalytic species. The linker can be an optionally substituted bivalent chemical group. The optionally substituted bivalent chemical group can comprise $R_n$ groups, with n being the number of R groups and being an integer of at least 1, preferably, not greater than 30, and, more preferably, not greater than 15. Generally, the bivalent chemical group is about 1 to about 30 atoms, preferably, about 1 to about 20 atoms, and, more preferably, about 5 to about 15 atoms, in length measured from the catalytic species to the support surface.

The linker can be selected from the group consisting of: —C($R_1$)H—, —C($R_2$)=C($R_3$)— and —C≡C—, where $R_1$, $R_2$ and $R_3$ are, independently, hydrogen, alkyl, substituted alkyl, cycloalkyl, substituted cycloalkyl, alkenyl, substituted alkenyl, cycloalkenyl, substituted cycloalkenyl, alkynyl, substituted alkynyl, cycloalkynyl, substituted cycloalkynyl, aryl, substituted aryl, aralkyl or substituted aralkyl. The R groups above may be optionally replaced with —O—, —S—, carbonyl, thiocarbonyl, —OC(O)—, —C(O)O—, —SC(O)—, —C(O)S—, —OC(S)—, —C(S)O—, —C(S)S—, —SC(S)—, —N($R_4$)—, —N($R_4$)C(O)—, —C(O)N($R_4$)—, —C($R_5$)=N—, —N=C($R_5$)—, —C($R_5$)=NO—, —ON=C($R_5$)—, —P—, —P(OH)O—, arylene, substituted arylene, cycloalkylene, substituted cycloalkylene, cycloalkenylene, substituted cycloalkenylene, bivalent heterocycle or bivalent substituted heterocycle, wherein $R_4$ and $R_5$ are, independently, hydrogen, alkyl, substituted alkyl, cycloalkyl, substituted cycloalkyl, alkenyl, substituted alkenyl, cycloalkenyl, substituted cycloalkenyl, alkynyl, substituted alkynyl, cycloalkynyl, substituted cycloalkynyl, aryl, substituted aryl, aralkyl or substituted aralkyl. Illustrative of the linker is a hydrocarbyl group comprising $R_n$ groups, wherein n is described above, and at least one R group is —$CH_2$—, and (n−1)—R— groups are optionally replaced with the R groups mentioned above, e.g., —O—, —S—, etc.

The term "substituted" is used herein to mean containing pendent substituent groups that do not alter the predominant chemical character of the substituted R group, e.g., hydrocarbon character for hydrocarbyls.

The term "alkyl" refers to a saturated branched or unbranched hydrocarbyl radical, preferably, those of about 1 to about 30, more preferably, those of about 1 to about 20 and, even more preferably, those of about 1 to about 6, carbon atoms. Examples of "alkyl" groups include, but are not limited to, methyl, ethyl, n-propyl, isopropyl, n-butyl, sec-butyl, isobutyl, tert-butyl, n-pentyl, 1-methylbutyl, 2-methylbutyl, isopentyl, neopentyl, 1,1-dimethylpropyl, n-hexyl, 1-methylpentyl, 2-methylpentyl, 3-methylpentyl, 1,1-dimethylbutyl, 2,2-dimethylbutyl, isohexyl and neohexyl groups.

The term "cycloalkyl" refers to a saturated cyclic hydrocarbyl radical, preferably, of about 3 to about 10, and, more preferably, of about 3 to about 6, carbon atoms. Examples of "cycloalkyl" groups include, but are not limited to, cyclopropyl, cyclobutyl, cyclopentyl, cyclohexyl, bicycloheptyl and decalin groups.

The term "alkenyl" refers to a branched or unbranched hydrocarbyl radical having at least one C=C bond, wherein the hydrocarbyl radical is, preferably, about 2 to about 30, more preferably, about 2 to about 20 and, even more preferably, about 2 to about 6, carbon atoms. Examples of "alkenyl" groups include, but are not limited to, vinyl, allyl, 1-propenyl, isopropenyl, 2-butenyl, 1,3-butadiene, 3-pentenyl and 2-hexenyl groups.

The term "cycloalkenyl" refers to a cyclic hydrocarbyl radical, preferably, of about 3 to about 10, and, more preferably, of about 3 to about 6, carbon atoms having at least one C=C bond.

The term "alkynyl" refers to a branched or unbranched hydrocarbyl radical, preferably, of about 2 to about 30, more preferably, of about 2 to about 20, and, even more preferably, of about 2 to about 6, carbon atoms having at least one C≡C bond. Examples of "alkynyl" groups include, but are not limited to, ethynyl, 1-propynyl, 2-propynyl, 2-butynyl, 3-butynyl and 2-pentene-4-ynyl groups.

The term "cycloalkynyl" refers to a cyclic hydrocarbyl radical, preferably, of about 3 to about 10, and, more preferably, of about 3 to about 6, carbon atoms having at least one C≡C bond. Examples of "cycloalkynyl" groups include, but are not limited to, pentynyl and hexynyl groups.

The term "aryl" refers to an aromatic cyclic hydrocarbyl radical, preferably, of about 6 to about 14 carbon atoms. Examples of "aryl" groups include, but are not limited to, phenyl, naphthyl, anthracyl and phenanthryl groups, with phenyl being the preferred aryl group.

The term "aralkyl" refers to an alkyl radical substituted with one or more aryl radicals. Examples of "aralkyl" groups include, but are not limited to, benzyl, phenethyl, diphenylmethyl and trityl groups, with benzyl being the preferred aralkyl group.

The phrase "bivalent heterocycle" refers to bivalent cyclic radicals typically having about 3 to about 10, preferably, about 3 to about 7, and, more preferably, about 4 to about 6, ring atoms with about 1 to about 4 of the ring atoms being O, S or N atoms, or mixtures of O, S and/or N atoms. Examples of bivalent heterocycle groups include, but are not limited to, bivalent radicals of thiirene, oxirane, aziridine, 1H-aziridine, 2H-aziridine, 2H-thiete, thietane, 2H-oxete, oxetane, azete, azetidine, 1,2-oxazetidine, thiophene, furan, pyrrole, imidazole, oxazole, isoxazole, thiazole, isothiazole, pyrazole, 1,3-dioxolane, 1,2,3-thiadiazole, 1,3,4-thiadiazole, 1,2,4-thiadiazole, 1,2,3-oxadiazole, 1,2,4-oxadiazole, 1,3,4-oxadiazole, 1,2,5-oxadiazole, 1,2,3-triazole, 1,2,4-triazole, tetrazole, oxadiazole, pyridine, quinoline, isoquinoline, quinolizine, quinazoline, pteridine, carbazole, benzoxazole, 1,3-oxazine, 2H-1,3-oxazine, phenazine, phenothiazine, pyridazine, pyrimidine, pyrazine, benzo[b]furan, benzo[b]thiophene, indole, isoindole, indazole, purine, isobenzofuran, tetrahydrofuran, 1,4-dioxane, pyrrolidine, tetrahydropyran, 1,2-dihydropyridine, 1,4-dihydropyridine, piperidine, piperazine, morpholine, thiomorpholine, chroman, isochroman, chromene, 1H-azepine, 3H-azepine, 1,2-diazepine, 1,3-diazepine, 1,4-diazepine, triazepines and azocine groups.

The term "heteroaryl" refers to aromatic heterocyclic radicals.

The terms "alkylene," "alkenylene," "alkynylene," "cycloalkylene," "cycloalkenylene" and "arylene" are bivalent equivalents of the alky, alkenyl, alkynyl, cycloalkyl, cycloalkenyl and aryl radicals, respectively.

The phrase "substituted alkyl" refers to an alkyl substituted with about 1 to about 5, and, preferably, about 1 to about 3, substituents selected from the group consisting of: hydroxy, sulfydryl, alkoxy, alkylthio, amino, alkylamino, dialkylamino, arylamino, N,N-arylalkylamino, diarylamino, azido, amidino, ureido, fluoro, chloro, bromo, iodo, nitro, cyano, acyl (preferably, acetyl and benzoyl), thioacyl, alkylsulfinyl, alkylsulfonyl, alkylsulfonamido, alkylsulfamoyl, carboxyl, alkylcarbonyloxy (preferably, acetoxy), arylcarbonyloxy (preferably, benzoyloxy), alkoxycarbonyloxy, aryloxycarbonyloxy, carbamoyl, aryl (preferably, phenyl), styryl, cycloalkyl, cycloalkenyl and heterocycle (preferably, heteroaryl).

The phrase "substituted alkenyl" refers to an alkenyl substituted with about 1 to about 5, and, preferably, about 1 to about 3, substituents selected from the group consisting of: hydroxy, sulfydryl, alkoxy, alkylthio, amino, alkylamino, dialkylamino, arylamino, N,N-arylalkylamino, diarylamino, azido, amidino, ureido, fluoro, chloro, bromo, iodo, nitro, cyano, acyl (preferably, acetyl and benzoyl), thioacyl, alkylsulfinyl, alkylsulfonyl, alkylsulfonamido, alkylsulfamoyl, carboxyl, alkylcarbonyloxy (preferably, acetoxy), arylcarbonyloxy (preferably, benzoyloxy), alkoxycarbonyloxy, aryloxycarbonyloxy, carbamoyl, aryl (preferably, phenyl), styryl, cycloalkyl, cycloalkenyl and heterocycle (preferably, heteroaryl).

The phrase "substituted alkynyl" refers to an alkynyl substituted with about 1 to about 5, and, preferably, about 1 to about 3, substituents selected from the group consisting of: hydroxy, sulfydryl, alkoxy, alkylthio, amino, alkylamino, dialkylamino, arylamino, N,N-arylalkylamino, diarylamino, azido, amidino, ureido, fluoro, chloro, bromo, iodo, nitro, cyano, acyl (preferably, acetyl and benzoyl), thioacyl, alkylsulfinyl, alkylsulfonyl, alkylsulfonamido, alkylsulfamoyl, carboxyl, alkylcarbonyloxy (preferably, acetoxy), arylcarbonyloxy (preferably, benzoyloxy), alkoxycarbonyloxy, aryloxycarbonyloxy, carbamoyl, aryl (preferably, phenyl), styryl, cycloalkyl, cycloalkenyl and heterocycle (preferably, heteroaryl).

The phrase "substituted cycloalkyl" refers to a cycloalkyl substituted with about 1 to about 5, and, preferably, about 1 to about 3, substituents selected from the group consisting of: alkyl, alkenyl, alkynyl, aralkyl, hydroxy, sulfydryl, alkoxy, alkylthio, amino, alkylamino, dialkylamino, arylamino, N,N-arylalkylamino, diarylamino, azido, amidino, ureido, fluoro, chloro, bromo, iodo, nitro, cyano, acyl (preferably, acetyl and benzoyl), thioacyl, alkylsulfinyl, alkylsulfonyl, alkylsulfonamido, alkylsulfamoyl, carboxyl, alkylcarbonyloxy (preferably, acetoxy), arylcarbonyloxy (preferably, benzoyloxy), alkoxycarbonyloxy, aryloxycarbonyloxy, carbamoyl, aryl (preferably, phenyl), styryl, cycloalkyl, cycloalkenyl and heterocycle (preferably, heteroaryl).

The phrase "substituted cycloalkenyl" refers to a cycloalkenyl substituted with about 1 to about 5, and, preferably, about 1 to about 3, substituents selected from the group consisting of: alkyl, alkenyl, alkynyl, aralkyl, hydroxy, sulfydryl, alkoxy, alkylthio, amino, alkylamino, dialkylamino, arylamino, N,N-arylalkylamino, diarylamino, azido, amidino, ureido, fluoro, chloro, bromo, iodo, nitro, cyano, acyl (preferably, acetyl and benzoyl), thioacyl, alkylsulfinyl, alkylsulfonyl, alkylsulfonamido, alkylsulfamoyl, carboxyl, alkylcarbonyloxy (preferably, acetoxy), arylcarbonyloxy (preferably, benzoyloxy), alkoxycarbonyloxy, aryloxycarbonyloxy, carbamoyl, aryl (preferably, phenyl), styryl, cycloalkyl, cycloalkenyl and heterocycle (preferably, heteroaryl).

The phrase "substituted cycloalkynyl" refers to a cycloalkynyl substituted with about 1 to about 5, and, preferably, about 1 to about 3, substituents selected from the group consisting of: alkyl, alkenyl, alkynyl, aralkyl, hydroxy, sulfydryl, alkoxy, alkylthio, amino, alkylamino, dialkylamino, arylamino, N,N-arylalkylamino, diarylamino, azido, amidino, ureido, fluoro, chloro, bromo, iodo, nitro, cyano, acyl (preferably, acetyl and benzoyl), thioacyl, alkylsulfinyl, alkylsulfonyl, alkylsulfonamido, alkylsulfamoyl, carboxyl, alkylcarbonyloxy (preferably, acetoxy), arylcarbonyloxy (preferably, benzoyloxy), alkoxycarbonyloxy, aryloxycarbonyloxy, carbamoyl, aryl (preferably, phenyl), styryl, cycloalkyl, cycloalkenyl and heterocycle (preferably, heteroaryl).

The phrase "substituted aryl" refers to an aryl substituted with about 1 to about 5, and, preferably, about 1 to about 3, substituents selected from the group consisting of: alkyl, alkenyl, alkynyl, aralkyl, hydroxy, sulfydryl, alkoxy, alkylthio, amino, alkylamino, dialkylamino, arylamino, N,N-arylalkylamino, diarylamino, azido, amidino, ureido, fluoro, chloro, bromo, iodo, nitro, cyano, acyl (preferably, acetyl and benzoyl), thioacyl, alkylsulfinyl, alkylsulfonyl, alkylsulfonamido, alkylsulfamoyl, carboxyl, alkylcarbonyloxy (preferably, acetoxy), arylcarbonyloxy (preferably, benzoyloxy), alkoxycarbonyloxy, aryloxycarbonyloxy, carbamoyl, styryl, cycloalkyl, cycloalkenyl, aryl (preferably, phenyl) and heterocycle (preferably, heteroaryl).

The phrase "substituted heterocycle" refers to a heterocycle radical substituted with about 1 to about 5, and, preferably, about 1 to about 3, substituents selected from the group consisting of: alkyl, alkenyl, alkynyl, aralkyl, hydroxy, sulfydryl, alkoxy, alkylthio, amino, alkylamino, dialkylamino, arylamino, N,N-arylalkylamino, diarylamino, azido, amidino, ureido, fluoro, chloro, bromo, iodo, nitro, cyano, acyl (preferably, acetyl and benzoyl), thioacyl, alkylsulfinyl, alkylsulfonyl, alkylsulfonamido, alkylsulfamoyl, carboxyl, alkylcarbonyloxy (preferably, acetoxy), arylcarbonyloxy (preferably, benzoyloxy), alkoxycarbonyloxy, aryloxycarbonyloxy, carbamoyl, aryl (preferably, phenyl), styryl, cycloalkyl, cycloalkenyl and heterocycle (preferably, heteroaryl).

The phrases "substituted arylene," "substituted cycloalkylene," "substituted cycloalkenylene" and "substituted bivalent heterocycle" refer to bivalent equivalents of substituted aryls, substituted cycloalkyls, substituted cycloalkenyls and substituted heterocycles, respectively.

The linkage connecting the linker to the support surface depends on the chemistry employed to react the linker and inorganic substance. The linkage can be an ether, thioether, ester, thioester, carbonate, carbamate, phosphate, phosphonate, phosphoester, phosphoramidate, amine, amide, imide, urea, thiourea, sulfonamide, sulfoxide, sulfone, disulfide, oxime, O-acyl oxime, O-carbamoyl oxime, O-acyloxyalkyl oxime, O-acyloxyalkyloxy oxime, O-oximinophosphate, O-oximinophosphonate, O-oximinophosphoramidate or C=C linkage. The linkage connecting the linker and catalytic species, e.g., enzyme can also be one of the aforementioned linkages.

The chemistry of reacting linkers to support surfaces is well described in the literature. See, e.g., Hermanson, G. T. et al., *Immobilized Affinity Ligand Techniques* (Academic Press, Inc., San Diego, Calif., 1992); Weetall, *Covalent Coupling Methods for Inorganic Support Materials*, in *Methods in Enzymology*, vol. XLIV, ed. Mosbach, K. (1976). The particular chemistry for reacting linkers to support surfaces clearly depends on the particular support material and linker employed. Likewise, the chemistry of reacting linkers to catalytic species depends on the particular linker and catalytic species employed. Specific examples of suitable linker/catalytic species coupling chemistry are shown in Table 1. According to Table 1, the catalytic species can be coupled to the linker via an amino, sulfhydryl, carbonyl or hydroxyl group or an active hydrogen atom on the catalytic species.

TABLE 1

Examples of Conventional Linker/Binding Moiety Coupling Chemistry

| Linkers Formed With | Catalytic Moiety Coupling Group |
|---|---|
| Cyanogen bromide (CNBr) | Amino |
| N-Hydroxy succinimide esters | Amino |
| Carbonyl diimidazole | Amino |
| Reductive amination | Amino |
| FMP activation* | Amino |
| EDC-mediated amide bond formation** | Amino |
| Organic sulfonyl chlorides: tosyl chloride and tresyl chloride | Amino |
| Divinylsulfone | Amino |
| Azlactone | Amino |
| Cyanuric chloride (trichloro-s-triazine) | Amino |
| Iodoacetyl or bromoacetyl activation methods | Sulfhydryl |
| Maleimide | Sulfhydryl |
| Pyridyl disulfide | Sulfhydryl |
| Divinylsulfone | Sulfhydryl |
| Epoxy | Sulfhydryl |
| TNB-Thiol*** | Sulfhydryl |
| Hydrazide | Carbonyl |
| Reductive amination | Carbonyl |
| Epoxy (bisoxirane) | Hydroxy |
| Divinylsulfone | Hydroxy |
| Cyanuric chloride | Hydroxy |
| Diazonium compounds | Active hydrogen |
| Mannich condensation | Active hydrogen |

*FMP means 2-fluoro-1-methyl-pyridinium toluene-4-sulfonate
**EDC means 1-ethyl-3-(3-dimethylaminopropyl) carbodiimide
***TNB-thiol means 2-iminothiolane 5,5-dithio-bis-(2-nitrobenzoic acid)

Catalytic Species

The inventive catalyst system further comprises at least one catalytic species, which is attached to a linker located on at least one surface of the support. The catalytic species is any molecule or molecule fragment capable of affecting the rate of a chemical reaction without itself being consumed or undergoing a chemical change. The catalytic species must be capable of being attached to the linker. Such catalytic species, include but are not limited to, enzymes, organometallic complexes, or other organic species, which are suitable to catalyze the reactions of interest.

In a preferred embodiment of the invention, the catalytic species is an enzyme. Suitable enzymes include, but are not limited to, enzymes selected from the enzymatic families including, but not limited to: oxidoreductases, transferases, hydrolases, lyases, isomerases and ligases. Exemplary enzymes from the oxidoreductase family, include, but are not limited to, P450 enzymes, reductases, peroxidases, hydrogenases, dehydrogenases and catalyses. Exemplary enzymes from the transferase family include, but are not limited to, glycosyltranserases and mannosyltransferases. Exemplary enzymes from the hydrolase family include, but are not limited to, esterases, glucoamylases, transcarbamylases, nucleases, ribonucleases, ATPases, peptidases, proteases and phosphodiesterases. Exemplary enzymes from the lyase family include, but are not limited to, polysaccharide lyases. Exemplary enzymes from the isomerase family include, but are not limited to, topoisomerases. Exemplary enzymes from the ligase family include, but are not limited to, snyntheteases. Additional enzymes include, but are not limited to, kinases, phosphoproteins and mutator transposons.

The enzymes that function, as the catalytic species may be naturally occurring or synthetic and in unmodified or modified form. Modifications include, but are not limited to, naturally occurring modifications and non-naturally occurring modifications, such as those created by DNA shuffling as described in U.S. Pat. Nos. 5,605,793, 5,811,238, 5,830,721, 6,117,679, 6,132,970, 6,165,793, 6,180,406, 6,238,884 and 5,965,408. The level of purity of the enzyme will depend upon the particular catalysis involved. Methods of purifying enzymes, both native and synthetic, and modified and unmodified, are well known in the art.

Another catalytic species envisioned for use in the present invention include organometallic complexes. Organometallic complexes are widely used as catalysts in the synthesis of fine chemicals and pharmaceuticals. Any organometallic complex that can be modified to react with an appropriate linker and attach to the support, can be used to realize the benefits of this invention. Suitable organometallic complexes include, but are not limited to, tetrakis(triphenylphosphine) palladium (0) for Heck arylations, (−)-1,2-Bis((2R, 5R)-2,5-dimethyl-phospholano)benzene, [DUPHOS] Rh(COD)$^+$ for asymmetric hydrogenation, 2-(Di-t-butylphosphino)biphenyl palladium for Suzuki coupling and synthesis of aromatic amines from arylhalides, and the like.

Still, another catalytic species envisioned for use in the present invention include an organic-based substance, e.g. an organic complexes or fragments. For instance, organic acids are used as catalysts in acid catalyzed hydrolysis reactions. Suitable organic-based catalytic species include, but are not limited to, formic acid, carboxylic acids, boron based Lewis acids, and Lewis bases such as pyridine, and the like.

Concentration of Components

Factors that determine concentrations of the $R_{10}$ groups and catalytic species include, but are not limited to, the identity of the $R_{10}$ group and catalytic species and the concentration of reactive sites, i.e., linkers, on the support surface.

In general, the $R_{10}$ group is present on at least one surface of the support in a sufficient amount such that when the surface is contacted with a composition comprising an enzyme, for example, non-specific binding of the enzyme to the support is reduced or prevented. In one embodiment of the invention, the concentration of the $R_{10}$ group is that amount sufficient to ensure a low surface charge, e.g. less than about 0.16 C/m$^2$, on the surface of the support. Preferably, the concentration of the $R_{10}$ group can be in the range of about 1 to about 10 groups per square nanometer (nm$^2$) of support surface area.

The catalytic species concentration depends primarily on the particular catalytic species employed. For example, an enzyme with a hydrodynamic radius of about 5 nm will generally "shadow" about 100 nm$^2$ of surface area. The enzyme is not always attached to a single linker in a one to one stoichiometry, but may be attached by several linker groups, e.g., when the enzyme is a large molecule. In embodiments employing smaller enzymes, less than stoichiometric amounts of the enzyme may be used and any unreacted linker groups may be "capped" to avoid interference during catalysis and optional enzyme separation.

Alternatively, the concentrations of $R_{10}$ groups and catalytic species may be stated in terms of how many functional groups on the support surface are reacted or "covered" by the $R_{10}$ groups and catalytic species (preferably, via linkers). For example, about 50% to about 99% of surface hydroxyl groups of the support material may be covered with $R_{10}$ groups and about 1% to about 50% of the surface hydroxyl groups may be covered with a catalytic species attached to the surface via linkers. In certain embodiments of the inventive catalyst system, about 75% to about 99% of surface hydroxyl groups on the support material is covered with $R_{10}$ groups and about 1% to about 25% of the surface hydroxyl groups is covered with a catalytic species attached to the surface via linkers.

The concentration of linker groups on the support surface can vary. In certain embodiments of the present invention, the catalytic species, e.g., enzyme, can "shadow" large regions of the support surface area if the catalytic species is a large moiety, as noted above. As a result, the concentration of the linkers on the support does not need to be relatively high. Basically, support surface area not coated with linkers is coated with $R_{10}$ groups to prevent the binding of the catalytic species to the support surface. In a preferred embodiment, a significant amount of the support surface is covered by $R_{10}$ groups, e.g. at concentrations of about 1 to about 10 groups per nm² on the surface of the support, and the remainder covered by linkers. Generally, the concentration of the linker will be an amount sufficient to provide sufficient catalytic species to catalyze the desired reaction. Typically, the concentration of the linker will range from about 0.1 to about 5.0 nm² of linker on the surface of the support.

The concentrations of linker groups, $R_{10}$ groups and catalytic species depend upon the particular reaction parameters and can be readily determined by the skilled artisan.

Preparing the Supported Catalyst Systems

Generally, the supported catalyst systems of the present invention are prepared by modification of at least one surface of a support to attach at least one $R_{10}$ group and a linker directly or indirectly to at least one surface of the support, and thereafter reacting the linker to form a catalytic species bound to the linker. The order of adding linkers to the support surface in conjunction with adding $R_{10}$ groups to the support surface can vary. The $R_{10}$ group can be created on the support surface after attaching the linker or it can be created prior to attaching the linker. Alternatively, precursors to either the $R_{10}$ group or the linker or both can be created and/or first attached and thereafter, reacted to create the final $R_{10}$ group and/or linker. Once the linker/$R_{10}$ group order is determined, the linker is chemically attached to the surface of the support using suitable coupling techniques and subsequently attached to the catalytic species with a secondary coupling procedure.

Preferably, supported catalyst systems of the invention are prepared by reacting an inorganic support material with a linker having at least two ends, in a manner sufficient to attach at least one end of the linker to least one surface of the support, and thereafter reacting at least one functional group on the support surface with an $R_{10}$ group or a reactant capable of forming a $R_{10}$ group, to create at least one $R_{10}$ group, on the at least one surface of the support. The desired catalytic species is then reacted with the linker such that the catalytic species is attached to the modified surface of the support, but, simultaneously is free and unconstrained as described hereinabove.

In a more preferred embodiment of the invention, the method of preparing supported catalyst systems of the present invention comprise the following steps: (1) contacting an inorganic support having reactive surface sites capable of non-selective binding with a linker, or a linker precursor, at an appropriate surface concentration to provide a modified support having a portion of its reactive surface sites attached to the linker or linker precursor; (2) contacting the modified support with a sufficient amount of a precursor to the $R_{10}$ group to cover the remainder of the reactive surface sites on the support; (3) converting the $R_{10}$ group precursor to the $R_{10}$ group; (4) optionally, converting the linker precursor to the linker; and (5) immobilizing the catalytic species to the linker. Using this process, the support surface is modified so that it has linkers which bind the catalytic species while the rest of the surface is covered with the $R_{10}$ groups to eliminate non-selective binding. Steps (1) and (2) above are most conveniently performed using silanizing agents, where the appropriate triethoxiysilane is reacted with surface hydroxyls of the inorganic support, such as silanol groups from a silica support, under reflux conditions in an appropriate solvent, such as toluene. Silanization chemistry is well known to one skilled in the art.

An exemplary linker precursor is aminopropyltriethoxysilane, which can be reacted with glutaraldehyde to form the linker after the silane has reacted with the surface of the inorganic support. The amino aldehyde reaction to form linkers is well known to one skilled in the art as discussed above.

An exemplary $R_{10}$ precursor is acetoxymethyltriethoxysilane, which can be later converted to the $R_{10}$ group —$CH_2OH$ by hydrolysis of the acetoxy group, see FIG. 17.

Figure 16:
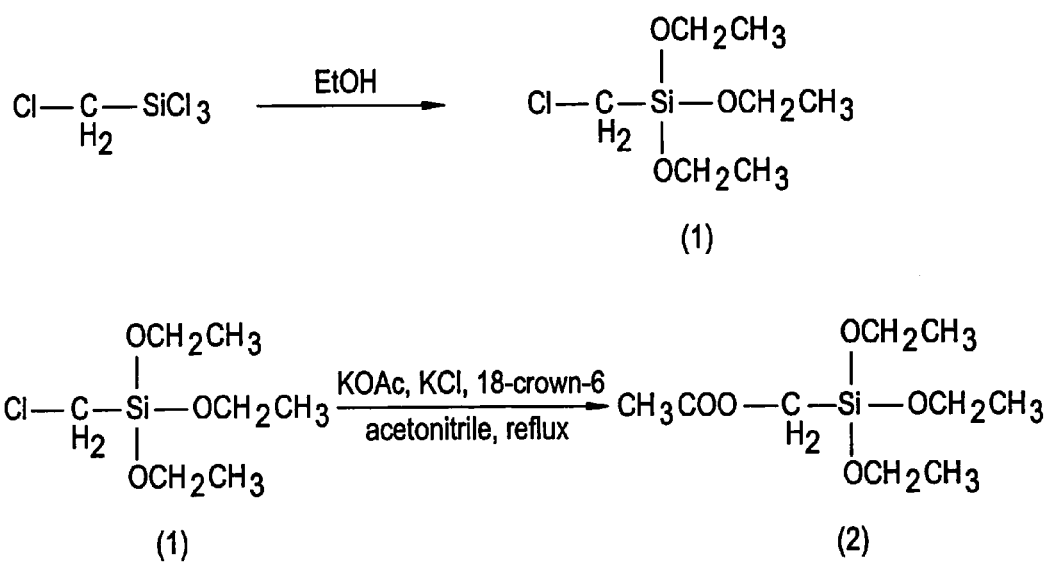
FIG. 16 depicts the preparation of a coating agent that yields —$CH_2OH$ as $R_{10}$, from the reaction illustrated in FIG. 17.
Figure 20:
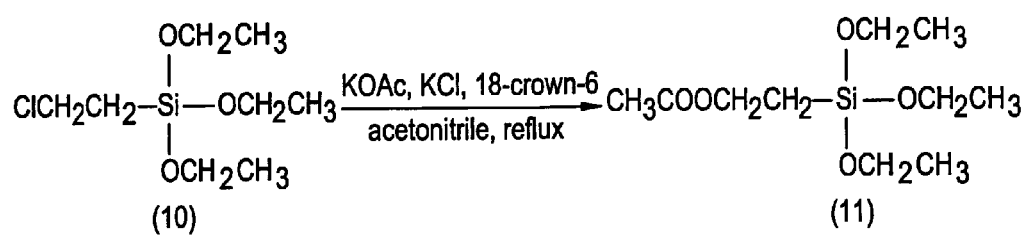
FIG. 20 shows the preparation of a coating agent that yields hydroxyethyl as $R_{10}$, from a reaction scheme similar to schemes illustrated in FIGS. 17 and 19.
Figure 21:
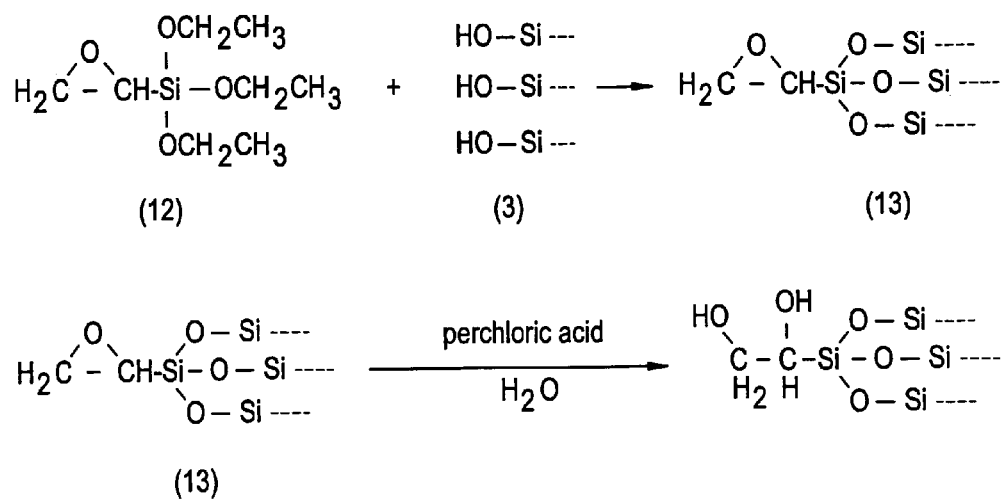
FIG. 21 shows a method for the preparation of a catalyst comprising silica and —Si—$R_{10}$ groups attached to the surface, wherein $R_{10}$ is indirectly attached to the surface via a silicon atom, which is not a part of the silica. $R_{10}$ is 1,2-dihydroxyethyl.
Figure 22:
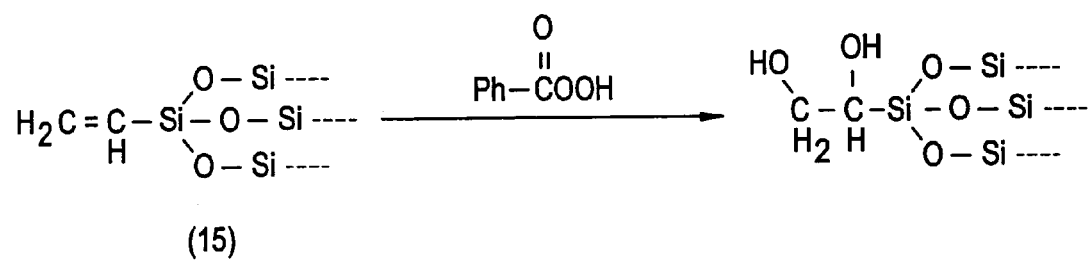
FIG. 22 shows another method for preparing a solid comprising silica and —Si—$R_{10}$ groups attached to the surface, wherein $R_{10}$ is indirectly attached to the surface via a silicon atom, which is not a part of the silica. $R_{10}$ is 1,2-dihydroxyethyl.

A specific method for preparing a silica support having —$CH_2OH$ as the $R_{10}$ group located on the silica surface is shown in FIGS. 16 and 17. FIG. 16 depicts the preparation of the coating agent, acetoxymethyltriethoxysilane (Compound (2)), which is used to introduce hydroxymethyl groups ($R_{10}$ groups) to silanol groups on the surface of silica. See the reactions presented in FIG. 17 wherein Compound (5) is silica having hydroxymethyl groups ($R_{10}$ groups) directly attached to the surface.

A method for preparing a silica surface comprising the $R_{10}$ group —$CH(OH)_2$ is shown in FIGS. 18 and 19. FIG. 18 depicts the preparation of the coating agent, diacetoxymethyltriethoxysilane (Compound (7)), used to introduce —$CH(OH)_2$ as the $R_{10}$ group to the silica surface. See the reactions and Compound (9) presented in FIG. 19.

FIG. 23 shows a method for preparing the coating agent, acetoxyethyltriethoxysilane (Compound (11)), used to introduce the $R_{10}$ group 2-hydroxyethyl to a silica surface.

Two methods for preparing a support comprising silica and 1,2-dihydroxyethyl as the $R_{10}$ group are depicted in FIGS. 24 and 25.

Once the support surface has been modified to attach linker and $R_{10}$ groups as appropriate, a sufficient amount of the chosen catalytic species is reacted with the linker. If the catalytic species is an enzyme, conventional methods of protein immobilization may be used. See, for example, G. T. Hermanson et al., *Immobilized Affinity Ligand Techniques*, (Academic Press). Other catalytic species, such as organometallic complexes or organic complexes, may require different chemical routes for immoblization. For example, an organometallic complex may have a pendant group attached to it terminating in an alpha olefin. The olefin can then react with a hydrotriethoxysilane via a hydrosilation reaction. The resultant organometallic-pendant-triethoxysilane can then react with the support, thereby attaching the organometallic to the support. See, e.g., Cornils et. al., *Applied Homogenous Catalysis with Organometallic Compounds* (Volume 3) (Wiley-VHC, 2002); and DeVos, D. E. et al., *Chiral Catalyst Immobilization and Recycling* (Wiley-VC, 2002).

The methods described above are general. The parameters and steps of the particular method employed will depend upon the specific support material, catalytic species, $R_{10}$ group, linker, and reactant molecule(s). The general steps described herein may be altered by methods known in the art, repeated or deleted if found to be unnecessary.

Supported catalyst systems of the invention may be used as catalysts to catalyze reactions generally known in the art to be catalyzed by the corresponding free catalytic species. For example, where the catalytic species is an enzyme, the supported catalyst system may be used to catalyze various reactions, including, but not limited to, oxidation/reduction reactions; the transfer of groups of atoms, e.g. amino, acetyl, phosphoryl, and glycosyl groups; hydrolytic cleavage of bonds; non-hydrolytic cleavage of, for example, C—C, C—O or C—N bonds; isomerization and transfer reactions; the covalent joining of two molecules coupled with the hydrolysis of an energy rich bond in ATP or similar triphosphates; and the like. When the catalytic species is an organometallic complex, the supported catalyst system may be used to catalyze reactions including, but not limited to, Heck arylations; Suzuki coupling reaction; synthesis of aromatic amines from arylhalides; and the like.

A major advantage of supported catalyst systems of the invention is the ease of recovery of the catalyst systems from a reaction mixture after reaction of reactants in the mixture to obtain the desired product. Catalytic species which are soluble in the reaction, such as enzymes or organometallic complexes, are typically very difficult to separate and recover. However, supported catalyst systems in accordance with the present invention are easily separated by conventional solid-liquid separation techniques, such as, for example, filtration or centrifugation, for recovery and re-use.

Supported catalyst systems in accordance with the present invention may be used in conventional reactors such as, for example a fixed (column) or fluidized bed reactors to catalyst a reaction. The catalysts may be used in a continuous or batch mode.

To further illustrate the present invention and the advantages thereof, the following specific examples are given. The examples are given as specific illustrations of the claim invention. It should be understood, however, that the invention is not limited to the specific details set forth in the examples.

All parts and percentages in the examples, as well as in the remainder of the specification, are by weight unless otherwise specified.

Further, ranges of numbers recited in the specification or claims, such as that representing a particular set of properties, units of measure, conditions, physical states or percentages, is intended to literally incorporate expressly herein by reference or otherwise, any number falling within such range, including any subset of numbers within any range so recited, as well as any obvious variations thereof.

EXAMPLES

Examples 1 and 2

Non-Specific Binding on Conventional Silica Media

These examples show that the neat uncoated charged silica surface of the prior art strongly adsorbs proteins based mostly on isoelectric point and the surface area of the silica. Two types of silicas were tested: Examples 1 and 2.

Example 1 is a low surface area silica gel with a surface area=161 m$^2$/g after 4 hours at 150° C. heat treat (micropore=73 m$^2$/g; mesopore=88 m$^2$/g; pore volume=0.373 cc/g; average pore diameter=93 Å).

Example 2 is a higher surface area/pore volume silica gel, surface area=253 m$^2$/g after 4 hours at 150° C. heat treat (micropore=35 m$^2$/g; mesopore=218 m$^2$/g; pore volume=2.445 cc/g; average pore diameter=387 Å).

The examples below describe a procedure wherein the neat silica samples of Examples 1 and 2 were contacted with a complex mixture of proteins in aqueous solution. The resultant supernatant was then analyzed by isoelectric focusing gel electrophoresis for protein adsorption.

A vial (325 µg protein/vial) of Pharmacia 3.6-9.3 Broad pI Calibration Kit (catalog #17-0471-01) was dissolved in 200 µl DI H$_2$O in an eppendorf tube. 0.005 g of the silica gel of Example 1 were added. In another eppendorf tube, a vial (325 µg protein/vial) of Pharmacia 3.6-9.3 Broad µl Calibration Kit (catalog #17-0471-01) was dissolved in 200 µl DI H$_2$O and then 0.005 g of the silica gel of Example 2 were added. Both samples were stirred end over end for 1 hour. These samples were run subjected to 3-9 Isoelectric Focusing Gel Electrophoresis on a Pharmacia PhastGel unit. The results are shown in FIG. 3.

| Lane | Description |
| --- | --- |
| 2, 7 | Pharmacia 3.6-9.3 Broad pI Standard |
| 3, 4 | Example 1 silica gel |
| 5, 6 | Example 2 silica gel |

Figure 3:
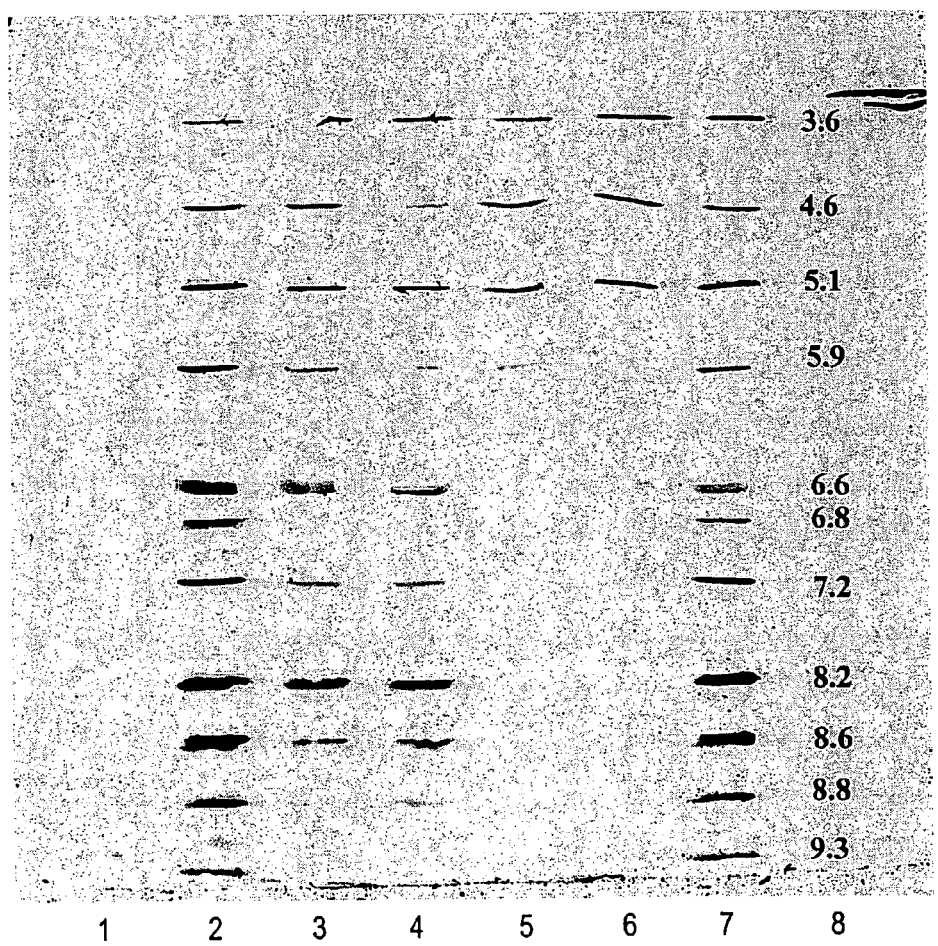
FIG. 3 shows the results of a pH 3-9 Isoelectric Focusing Gel Electrophoresis of Examples 1 and 2, with lanes 2 and 7 representing Pharmacia 3.6-9.3 Broad pI Standard, lanes 3 and 4 representing the support of Example 1 and lanes 5 and 6 representing the support of Example 2. This figure illustrates non-specific binding of untreated conventional inorganic oxide supports.

FIG. 3 shows that bands (proteins) were missing from the samples that were contacted with the silica gel supports of Examples 1 and 2, which means that the proteins adsorbed to the silica surfaces. The high surface area silica, Example 2, adsorbed all of the proteins with isoelectric points greater than 5.9, while the lower surface silica, Example 1, adsorbed only proteins of higher pI. The data clearly show that uncoated silica binds proteins primarily through a strong electrostatic interaction, and that the surface is negatively charged at this pH (assumed to be approximately 5.5).

Examples 3-5

Non-Selective Binding on Hydrophobic Supports

These examples show that when silica is coated with hydrophobic groups, or methyl or octyl groups, strong adsorption occurs, especially at moderate ion strength of the solvent (approximately 0.1 M NaCl).

The support of Example 3 is an uncoated neat commercial wide pore silica from W. R. Grace & Co., XWP-gel P 005, SA=72 m$^2$/g, with 50 nm pore median that had been activated for 2 hours at 150° C.

The support of Example 4 is the silica of Example 3 coated with methyl groups as described below.

The support of Example 5 is the silica of Example 3 coated with octyl groups as described below.

The support of Example 4 was prepared as follows: in a 250 ml round bottom flask, 50 ml toluene and 6.16 g of methyltriethoxysilane were added. Then 10.1 g of the silica of Example 3 were added to the toluene/methyltriethoxysilane solution. N$_2$ was flowed for 5 minutes to remove air and continued for the entire reaction. The sample was refluxed and stirred at 110° C. for 4 hours. The sample was then filtered and washed 3 times with 50 ml of toluene. The sample was reslurried into 50 ml of toluene, then filtered and washed 3 times with 50 ml of toluene. The sample was then reslurried into 50 ml of toluene, filtered and washed 3 times with 50 ml of toluene. The sample was dried at 110° C. and calcined for 4 hours at 150° C.

The support of Example 5 was prepared as follows: 10.1 g of the silica of Example 3 were impregnated to incipient wetness with 0.53 g of octyltriethoxysilane dissolved in 13.25 g of toluene as solvent. The sample was then air-dried in a hood for 2 hours, dried at 110° C. for one hour and calcined for 4 hours at 150° C.

Protein adsorption in 0.1 M NaCl was determined as follows: because the surfaces of the supports of Examples 4 and 5 were hydrophobic, a wetting procedure was needed to insure good contact with the protein solution. Thus, to an eppendorf tube, 0.014 g of the silica of Example 3 were added as the control. Then, 1.0 ml ethanol was added, stirred and centrifuged with supernatant removed. 0.5 ml ethanol and 0.5 ml DI $H_2O$ were added, stirred and centrifuged with supernatant removed. 0.25 ml ethanol and 0.75 ml DI $H_2O$ were added, stirred and centrifuged with supernatant removed. 1 ml DI $H_2O$ was added, stirred and centrifuged with supernatant removed. The DI $H_2O$ wash was repeated four more times. 1.0 ml 0.1 M NaCl+0.02 M PBS (pH 7.4) were added, stirred and centrifuged with supernatant removed. The wash with 0.1 M NaCl+0.02 M PBS was repeated four more times. Two vials of Sigma IEF Mix 3.6-9.3 Isoelectric Focusing Marker (catalog #I-3018) were dissolved into 500 µl 0.1 M NaCl+0.02 M PBS (pH 7.4). The dissolved IEF Mix was placed in an eppendorf tube.

To another eppendorf tube, 0.014 g of the support of Example 4 were added. The same wetting procedure and protein addition for Example 3 were performed with Example 4.

To a third eppendorf tube, 0.014 g of the support of Example 5 were added. The same wetting procedure and protein addition for Example 3 were performed with Example 5.

One vial of Sigma IEF Mix 3.6-9.3 Isoelectric Focusing Marker (catalog #I-3018) was dissolved into 250 µl 0.1 M NaCl+0.02 M PBS (pH 7.4). This was the standard untreated protein mixture.

All samples were stirred end over end for 1 hour. The samples were subjected to 3-9 Isoelectric Focusing Gel Electrophoresis on a Pharmacia PhastGel unit. The results are shown in FIG. 4.

| Lane | Description |
|------|-------------|
| 1, 8 | Standard protein mixture |
| 2, 3 | Example 3 silica |
| 4, 5 | Example 4 support |
| 6, 7 | Example 5 support |

Figure 4:
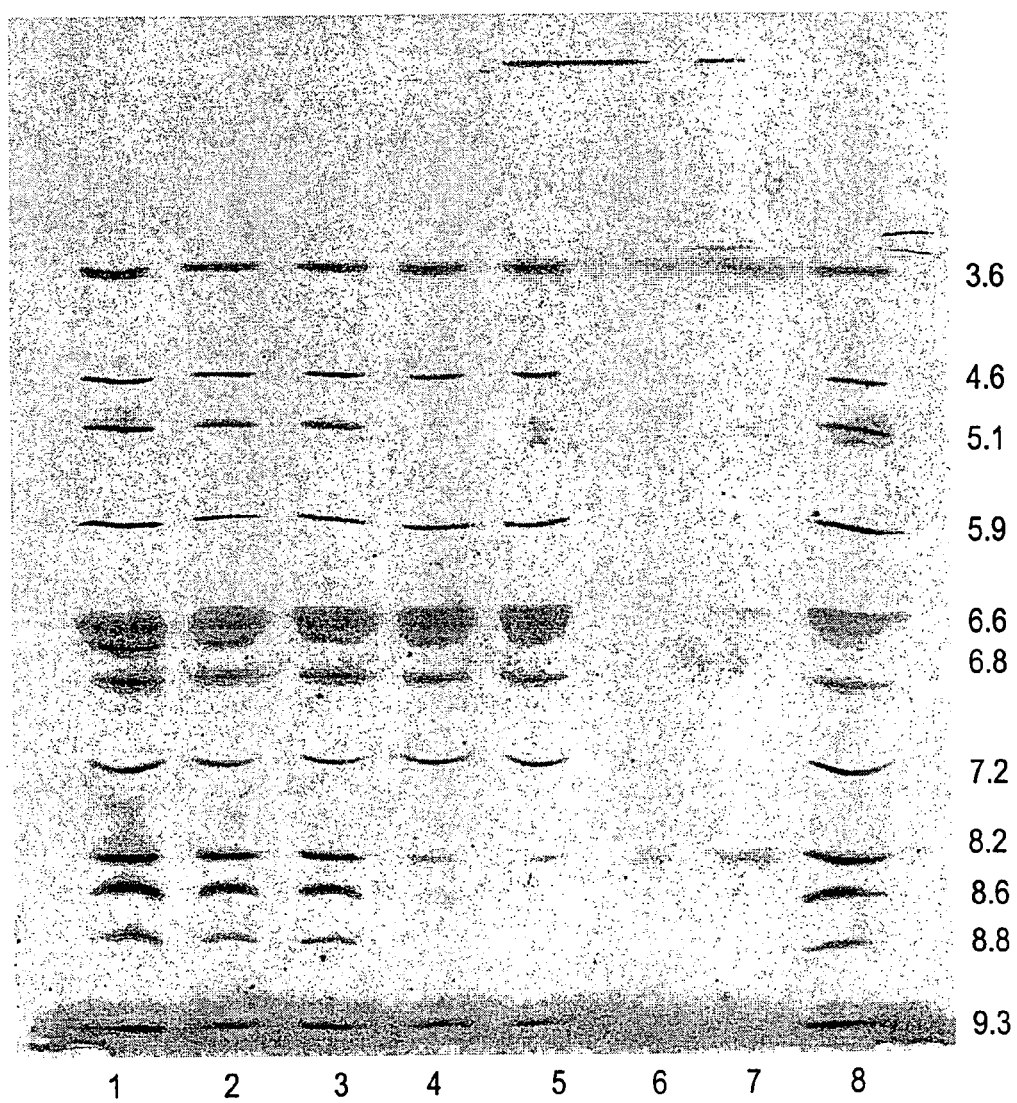
FIG. 4 shows the results of a pH 3-9 Isoelectric Focusing Gel Electrophoresis of Examples 3 through 5, with lanes 1 and 8 representing the standard protein mixture, lanes 2 and 3 representing the support of Example 3, lanes 4 and 5 representing the support of Example 4 and lanes 6 and 7 representing the support of Example 5.

As seen in FIG. 4, while the surface charge of the silica was "screened" by the dissolved salt, 0.1 M NaCl, and no protein binding occurred, the hydrophobic interaction of the methyl, and especially the octyl, groups was very strong and many of the bands were missing. The data show clearly that a hydrophobic surface composition can lead to non-selective binding.

Examples 6-8

Reducing Non-Selective Binding using an $R_{10}$ Group

Examples 6-8 show the advantage of employing an $R_{10}$ group according to the invention for reducing non-selective protein binding to a silica surface.

The support of Example 6 is the same as the silica of Example 3 except the silica was activated for 2 hours at 200° C.

The support of Example 7 is an intermediate surface composition, with the silica surface having Si—R groups attached, wherein R is acetoxymethyl.

The support of Example 8 is an example of the surface composition of the present invention, with the silica surface having Si—$R_{10}$ groups attached, wherein $R_{10}$ is methylhydroxy. The advantage of the surface of the support of Example 8 with high and low ionic strength solvents is also shown.

The support of Example 7 was prepared as follows: in a 250 ml round bottom flask, 50 ml toluene and 20.42 g of acteoxymethyltriethoxysilane were added. 15.05 g of the support of Example 6 were added to the toluene/acteoxymethyltriethoxysilane solution. $N_2$ was flowed for 5 minutes to remove air and continued for the entire reaction. The sample was refluxed and stirred at 110° C. for 16 hours. Then, the sample was filtered and washed 3 times with 50 ml of toluene. The sample was reslurried into 50 ml of toluene, filtered and washed 5 times with 50 ml of toluene. The sample was then reslurried into 50 ml of toluene, filtered and washed 5 times with 50 ml of toluene. It was dried at 110° C. and calcined for 4 hours at 150° C.

The support of Example 8 was prepared as follows: in a 250 ml round bottom flask, 10 g of the support of Example 7 and 100 ml 0.01 M $H_2SO_4$ were added. $N_2$ was flowed for 5 minutes to remove air and continued for the entire reaction. The sample was refluxed and stirred at 100° C. for 18 hours. Then, the sample was filtered and washed 2 times with 100 ml (80° C.) DI $H_2O$. The sample was reslurried into 100 ml (80° C.) DI $H_2O$, filtered and washed 2 times with 100 ml (80° C.) DI $H_2O$, dried at 110° C. and calcined for 4 hours at 150° C.

To an eppendorf tube, 0.007 g of the support of Example 7 were added. One vial of Sigma IEF Mix 3.6-9.3 Isoelectric Focusing Marker (catalog #I-3018) was dissolved into 250 µl 0.14 M NaCl+0.02 M PBS (pH 7.2) and then added to the eppendorf tube. The sample was labeled Example 7 high salt.

To a second eppendorf tube, 0.007 g of the support of Example 8 were added. One vial of Sigma IEF Mix 3.6-9.3 Isoelectric Focusing Marker (catalog #I-3018) was dissolved into 250 µl 0.14 M NaCl+0.02 M PBS (pH 7.2) and then added to the eppendorf tube. This sample was labeled Example 8 high salt.

To a third eppendorf tube, 0.007 g of the support of Example 7 were added. One vial of Sigma IEF Mix 3.6-9.3 Isoelectric Focusing Marker (catalog #I-3018) was dissolved into 250 µl 0.02 M PBS (pH 7.4) and then added to the eppendorf tube. This sample was labeled Example 7 low salt.

To a fourth eppendorf tube, 0.007 g of the support of Example 8 were added. One vial of Sigma IEF Mix 3.6-9.3 Isoelectric Focusing Marker (catalog #I-3018) was dissolved into 250 µl 0.02 M PBS (pH 7.4) and then added to the eppendorf tube. This sample was labeled Example 8 low salt.

To a fifth eppendorf tube, one vial of Sigma IEF Mix 3.6-9.3 Isoelectric Focusing Marker (catalog #I-3018) was dissolved into 250 µl DI $H_2O$. This sample was labeled protein mixture standard.

Figure 5:
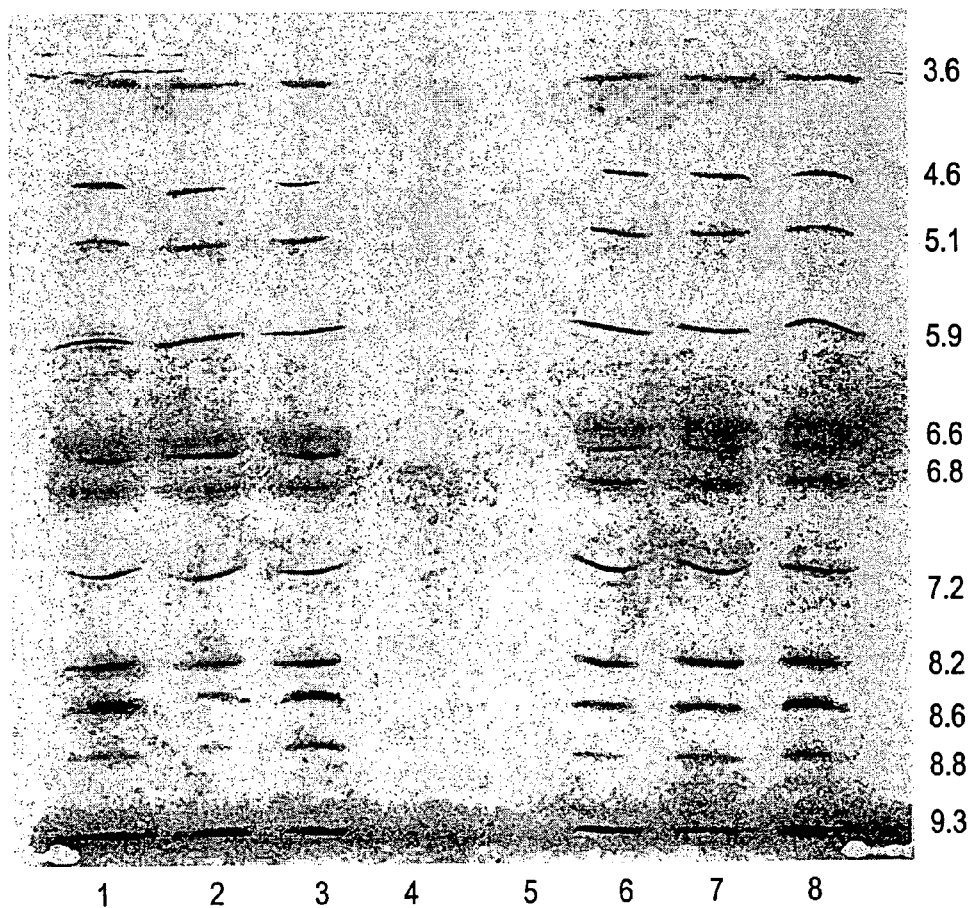
FIG. 5 shows the results of a pH 3-9 Isoelectric Focusing Gel Electrophoresis of Examples 6 through 8, with lanes 1 and 8 representing the standard protein mixture, lanes 2 representing the support of Example 7 (high salt), lane 3 representing the support of Example 8 (high salt), line 6 representing the support of Example 7 (low salt) and lane 7 representing the support of Example 8 (low salt).

All samples were stirred end over end for 1 hour. All samples were then subjected 3-9 Isoelectric Focusing Gel Electrophoresis on a Pharmacia PhastGel unit. The results are shown in FIG. 5.

| Lane | Description |
|------|-------------|
| 1, 8 | protein mixture standard |
| 2 | Example 7 high salt |
| 3 | Example 8 high salt |
| 6 | Example 7 low salt |
| 7 | Example 8 low salt |

The results of this experiment clearly show the ability of the support of Example 8 to avoid non-specific adsorption to the silica surface, in that all of the protein bands are present.

Characterization of Example 8

Figure 6:
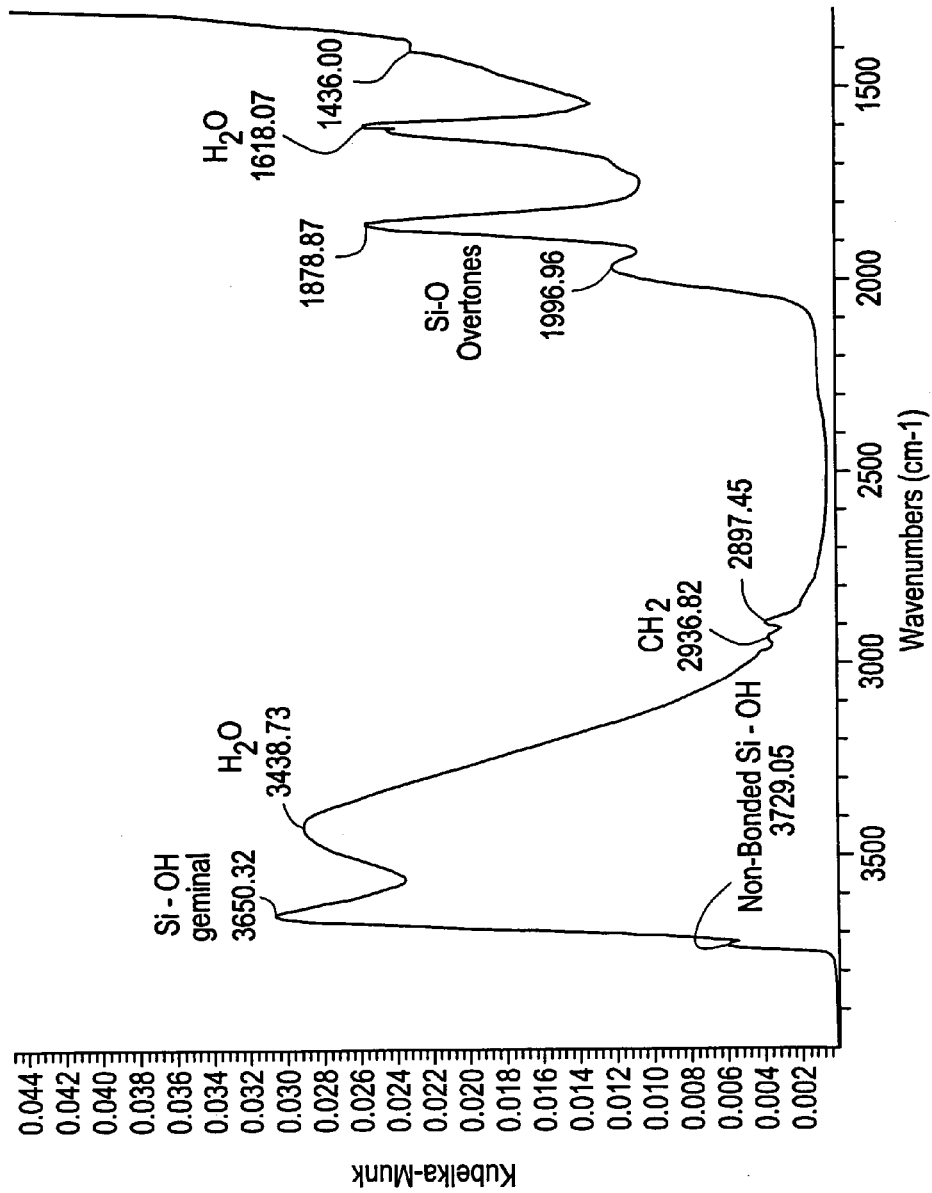
FIG. 6 shows the diffuse reflectance IR spectrum of the support of Example 8.
Figure 7:
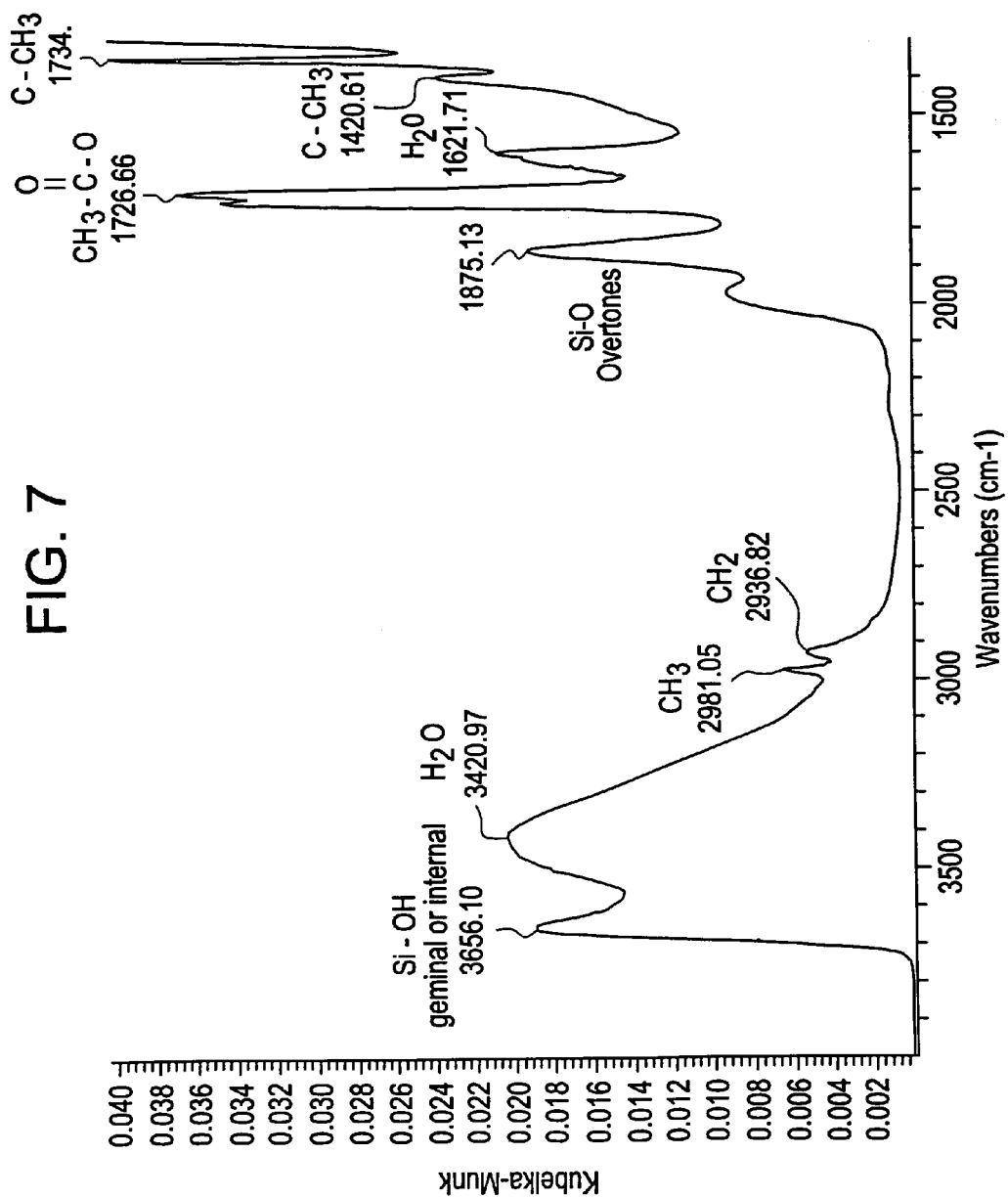
FIG. 7 shows the diffuse reflectance IR spectrum for the support of Example 7 following modification of the support to contain a $R_{10}$ precursor.

The surface composition of the support of Example 8 was characterized by analyses described below:

FIG. 6 shows the diffuse reflectance infrared spectrum of the support of Example 8, which had a surface composition comprising —$CH_2OH$ groups, from 1400-4000 $cm^{-1}$. The infrared data were acquired on a Nicolet Magna 550 using a Spectra-Tech diffuse reflectance accessory. The samples were diluted 1:20 in KBr with 512 scans collected at 4 $cm^{-1}$ resolution. The peaks at 2937 and 2897 $cm^{-1}$ clearly show the presence of the —$CH_2$ groups. The bands for the —OH resonances are buried under the broad peak at 3483 $cm^{-1}$. For comparison, FIG. 7 shows the spectrum of the support Example 7, with a surface composition comprising —$CH_2OCOCH_3$ groups. New resonances occurred at 1726, 1421, and 1374 $cm^{-1}$ which are characteristic resonances associated with acetoxy groups.

Figure 8:
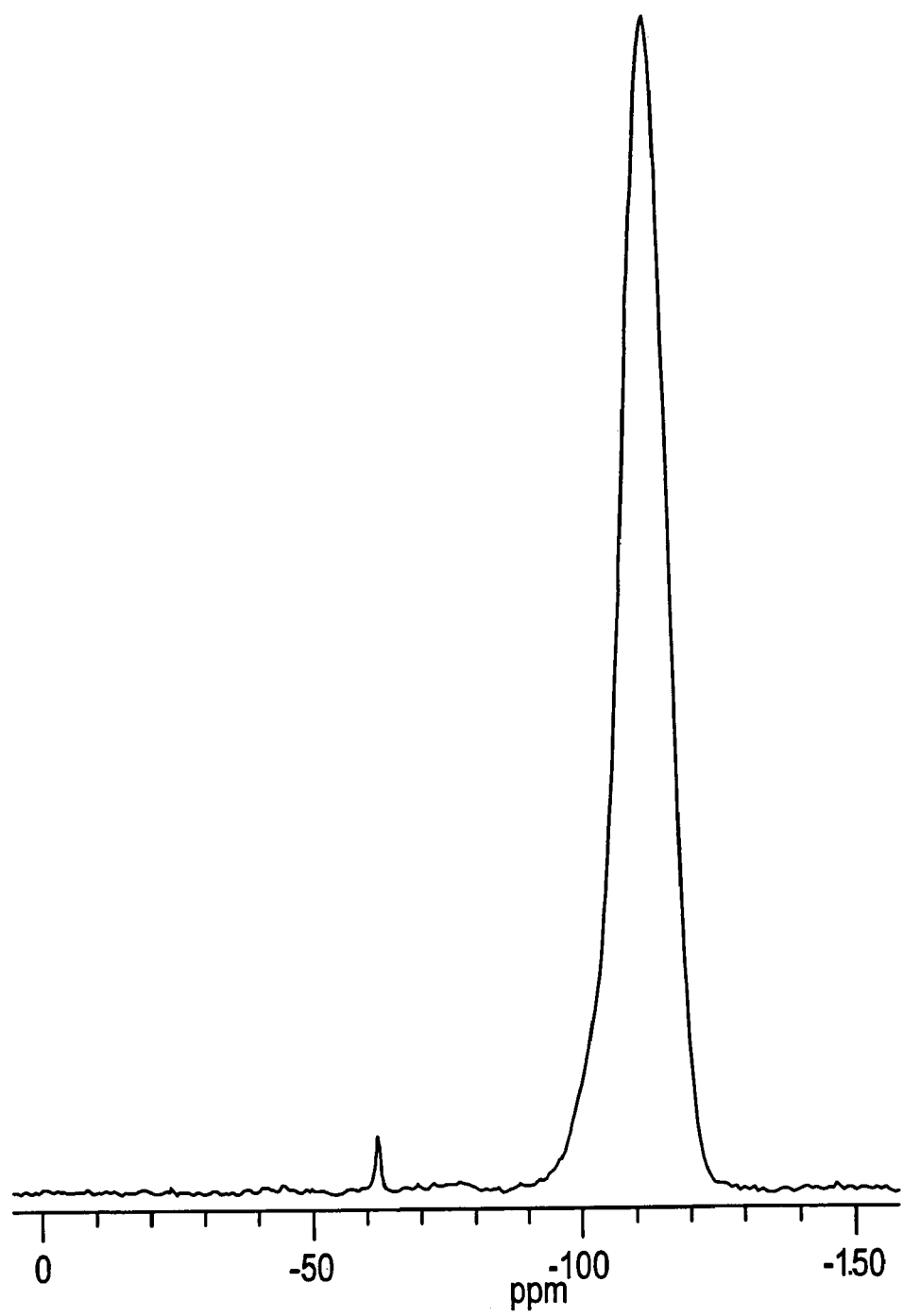
FIG. 8 shows the MAS $Si^{29}$ NMR spectrum of the support of Example 8 following modification of the support to contain a $R_{10}$ group.

FIG. 8 shows the MAS $Si^{29}$ NMR spectrum of the support of Example 8. A single-pulse $^{29}Si$ nuclear magnetic resonance experiment was performed on a Chemagnetics CMX 200 operating at a resonance frequency of 39.76 MHz. The sample was packed in a 14 mm pencil-style rotor. A pulse length of 4 μs corresponding to a 22 degree pulse was utilized along with a relaxation delay of 60 seconds. The clear resonance at −62 ppm has been identified as $O_3Si$—$CH_x$ (Sindorf. D. W. et al., *J. Am. Chem. Soc.* 105: 3767-3776 (1983)).

Figure 9:
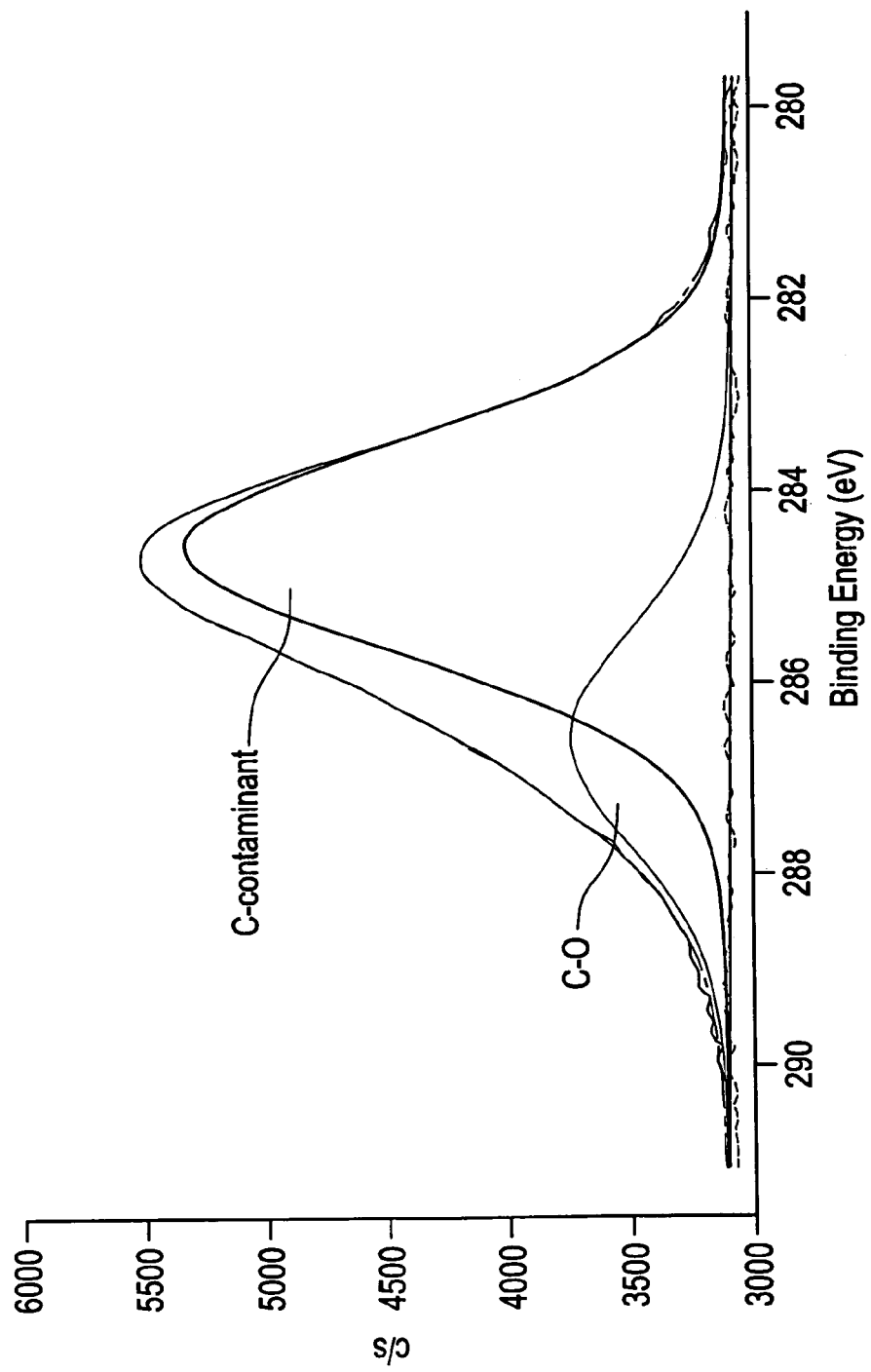
FIG. 9 shows the X-ray photoelectron spectrum (XPS) of the support of Example 8 following modification of the support to contain a $R_{10}$ group.
Figure 10:
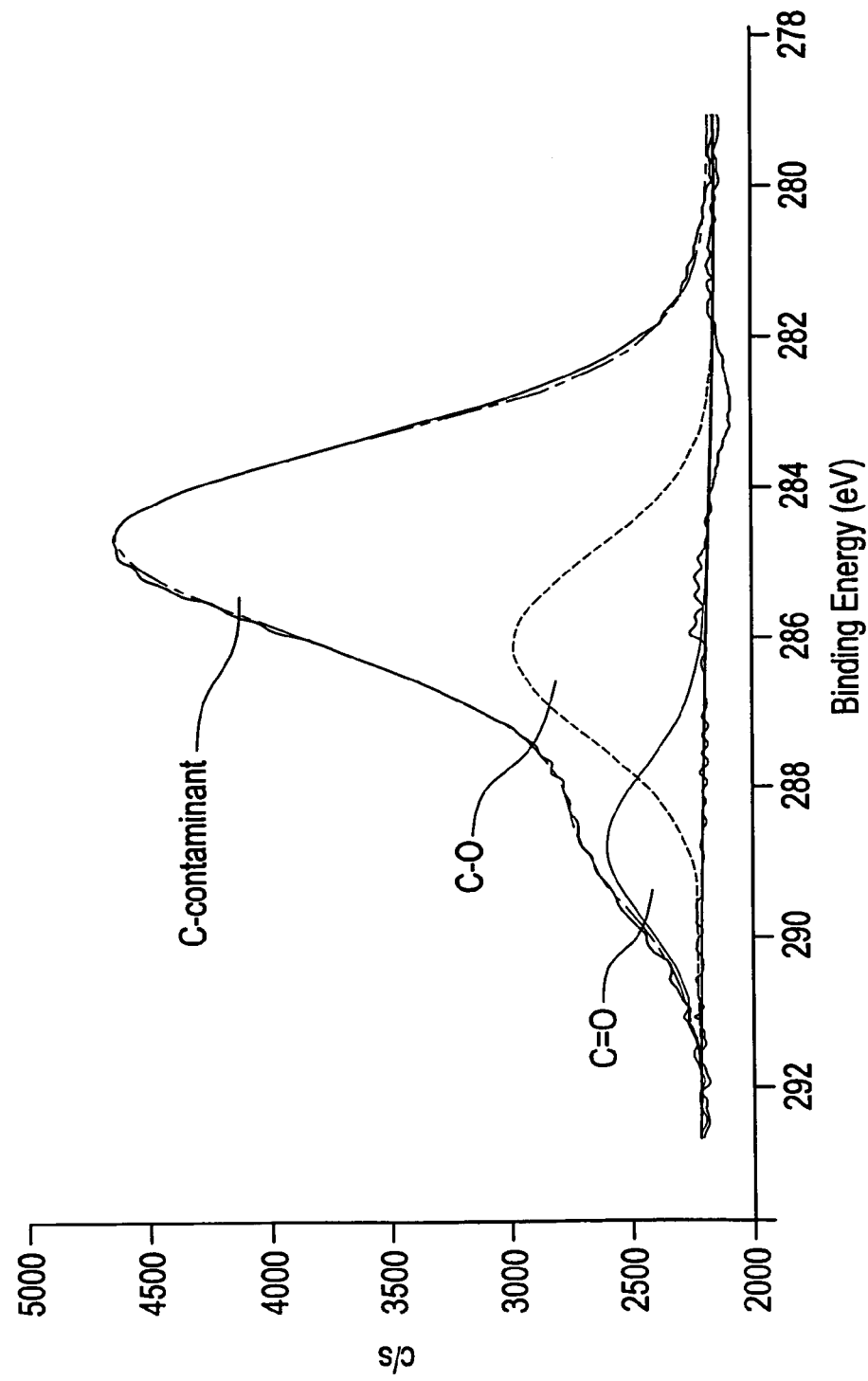
FIG. 10 shows the XPS spectrum of the support of Example 7 following modification of the support to contain a $R_{10}$ precursor.

FIG. 9 shows the x-ray photoelectron spectrum of the support of Example 8. The sample was mounted on a sample stub with double-sided tape and a 2 hour carbon, oxygen, and silicon scan was conducted. The spectrum was fit to two peaks which were identified as contaminant C, 284.7 eV, and an alcohol C atom, 286.7 eV. See, e.g., Moulder, J. F. et al., *Handbook of X-ray Photoelectron Spectroscopy*, Perkin-Elmer Corp., Eden Prairie, Minn. (1992). For comparison, the XPS spectrum of the support of Example 7 is shown in FIG. 10. In this case, a peak at 289 eV associated with the carboxyl carbon was also observed. These studies indicate that the surface composition of the support of Example 8 comprised methylhydroxy groups, i.e., —$CH_2OH$.

The concentration of $R_{10}$ groups (—$CH_2OH$) on the support of Example 8 was 2.01 groups/$nm^2$ and was calculated from the surface area of the silica support (72 $m^2/g$) carbon content (1.907%) of the final product. The surface area was measured using conventional BET surface area methodologies and the carbon content (% by weight) was measured using a model C-144 LECO Carbon Analyzer.

Examples 9 and 10

Unmodified (Ex. 9) and Modified (Ex. 10) Support Surfaces 850 g toluene and 13.37 g 3-aminopropyltriethoxysilane were added to a 2000 ml round bottom flask. Then, 200 g of silica (Grace Davison Silica Gel #2408, aged 40 hours at 100° C., calcined for 2 hours at 200° C.) were added to the round bottom flask, followed by the addition of 15 boiling chips. The round bottom flask was put in a heating mantle and attached condenser. The heating mantle was attached to the top of an orbital shaker, which was operated at a speed of 115 rpm. $N_2$ was passed through the round bottom flask and condenser to remove air during the entire reaction. The sample was refluxed for 4 hours and then, filtered and washed with 2×1000 ml toluene, dried at 115° C. and calcined for 2 hours at 150° C. This sample was labeled Intermediate A2.

206 g Intermediate A2 and 500 ml coupling buffer (0.1 M $Na_2PO_4$+0.15 M NaCl (pH 7.0)) were mixed in a 4000 ml beaker and stirred. In a 1000 ml beaker, 500 ml coupling buffer, 7.88 cc 50 wt. % glutaraldehyde and 30.96 g $NaCNBH_3$ were stirred together until dissolved. The glutaraldehyde-containing mixture was then added to the silica slurry (Intermediate A2-containing slurry) and stirred for 4 hours, filtered, washed with 1000 ml coupling buffer and reslurried in 2000 ml coupling buffer. This filter/wash/reslurry step was repeated two more times. The final product is Example 9 and was stored in 20% EtOH.

850 g toluene and 13.37 g 3-aminopropyltriethoxysilane were added to a 2000 ml round bottom flask. Then, 200 g of silica (Grace Davison Silica Gel #2408, aged 40 hours at 100° C., calcined for 2 hours at 200° C.) were added to the round bottom flask, followed by the addition of 15 boiling chips. The round bottom flask was put in a heating mantle and attached condenser. The heating mantle was attached to the top of an orbital shaker, which was operated at a speed of 115 rpm. $N_2$ was passed through the round bottom flask and condenser to remove air during the entire reaction. The sample was refluxed for 4 hours and then, filtered and washed with 2×1000 ml toluene, dried at 115° C. and calcined for 2 hours at 150° C. This sample was labeled Intermediate A3.

1600 ml 1.0 M NaCl were mixed with 215 g Intermediate A3 in a 2000 ml beaker and stirred with a magnetic stirrer. The initial pH was 8.66. 1.0 M HCl was added dropwise until the pH became 2.0. The pH was held at 2.0 for 15 minutes. The sample was filtered and washed with 5×1000 ml DI $H_2O$, dried at 115° C. and calcined for 2 hours at 200° C. This sample was labeled Intermediate B3.

680 g toluene and 441.68 g acetoxymethyltriethoxysilane were mixed in a 2000 ml round bottom flask. 206 g Intermediate B3 were then added along with 15 boiling chips. The round bottom flask was placed in a heating mantle and attached condenser. The heating mantle was attached to the top of an orbital shaker operating a speed of 115 rpm. $N_2$ was passed through the round bottom flask and condenser to remove air during the entire reaction. The sample was refluxed overnight (approximately 16 hours), filtered, washed with 3×1000 ml toluene, dried at 115° C. and calcined for 2 hours at 150° C. This sample was labeled Intermediate C3.

1000 ml 0.1 M HCl was added to a 2000 ml round bottom flask along with 212 g Intermediate C3. 15 boiling chips were put in the round bottom flask, which was placed in a heating mantle and attached condenser. The heating mantle was attached to the top of an orbital shaker operating at a speed of 115 rpm. $N_2$ was passed through the round bottom flask and condenser to remove air for the entire reaction. The sample was refluxed for 4 hours, filtered, washed with 3×1000 ml DI $H_2O$, dried at 115° C. and calcined for 2 hours at 150° C. This sample was labeled Intermediate D3.

208 g Intermediate D3 and 500 ml coupling buffer (0.1 M Na$_2$PO$_4$+0.15 M NaCl (pH 7.0)) were mixed in a 4000 ml beaker and stirred. 500 ml coupling agent were added to a 1000 ml beaker along with 7.88 cc 50 wt. % glutaraldehyde and 30.96 g NaCNBH$_3$. The mixture was stirred until dissolved and then added to the slurried Intermediate D3. The resultant mixture was stirred for four hours, filtered, washed with 1000 ml coupling buffer and reslurried in 2000 ml coupling buffer. The filter/wash/reslurry step was repeated two more times. The rewashed and reslurried sample was filtered and then washed with 1000 ml 20% EtOH. This filter/wash step was repeated two more times. The final product is Example 10 and was stored in 20% EtOH.

Example 11

Immobilization Procedure

An appropriate amount of the chosen enzyme was weighed out to yield the desired concentration (ranging from 0.05 to 1.0 mg protein/ml) in 100 ml coupling buffer (100 mM Na$_2$PO$_4$+150 mM NaCl (pH 7.0)). 1 g (silica basis) of the final product of Example 9 or Example 10 was added to the enzyme along with 126 mg NaCNBH$_3$. The reaction was allowed to shake at 150 rpm on a flatbed shaker at room temperature for 2 hours. The reaction was then filtered and the filtrate tested for remaining protein content using a BCA assay kit. The sample was washed with 100 ml coupling buffer at least twice, or until no protein activity was found in the filtrate (measured by tetrapeptide activity). Then, the sample was again placed in 100 ml of coupling buffer along with 126 mg NaCNBH$_3$ and allowed to shake at 150 rpm at room temperature for 2 hours. The sample was filtered, washed with 100 ml coupling buffer at least twice, and allowed to air dry under filtration suction. The sample was then dried in a 40° C. incubator for 20 minutes. Samples were stored in PTFE-capped glass vials.

Example 12

Catalysis: α-Chymotrypsin Hydrolytic
Reaction—Hydrolysis of a Tetrapeptide

An appropriate amount of immobilized α-chymotrypsin (CT) on the chosen support (Example 9 or 10) was placed in a 20 ml glass scintillation vial (2 mg preparations are used for most reactions). 10 ml of reaction buffer were added and the sample was allowed to equilibrate for 2 minutes. The hydrolytic substrate tetrapeptide N-succinyl-ala-ala-pro phe p-nitroanilide (Sigma #S-7388) (reactant molecule) was delivered to the reaction vessel in 200 µl DMF to a final tetrapeptide concentration of 0.1 mM (final DMF concentration 2% v/v). The reaction was allowed to proceed at room temperature on a flatbed shaker at 150 rpm. 1.5 ml aliquots were withdrawn and the increase in absorbance measured at 410 nm due to the liberation of p-nitroanilide at appropriate time intervals during the period in which total conversion remains below 10%. The aliquots were returned to the reaction vessel and the reaction allowed to continue. This process ensures that calculated initial rates are based on the linear reaction time period.

Figure 11:
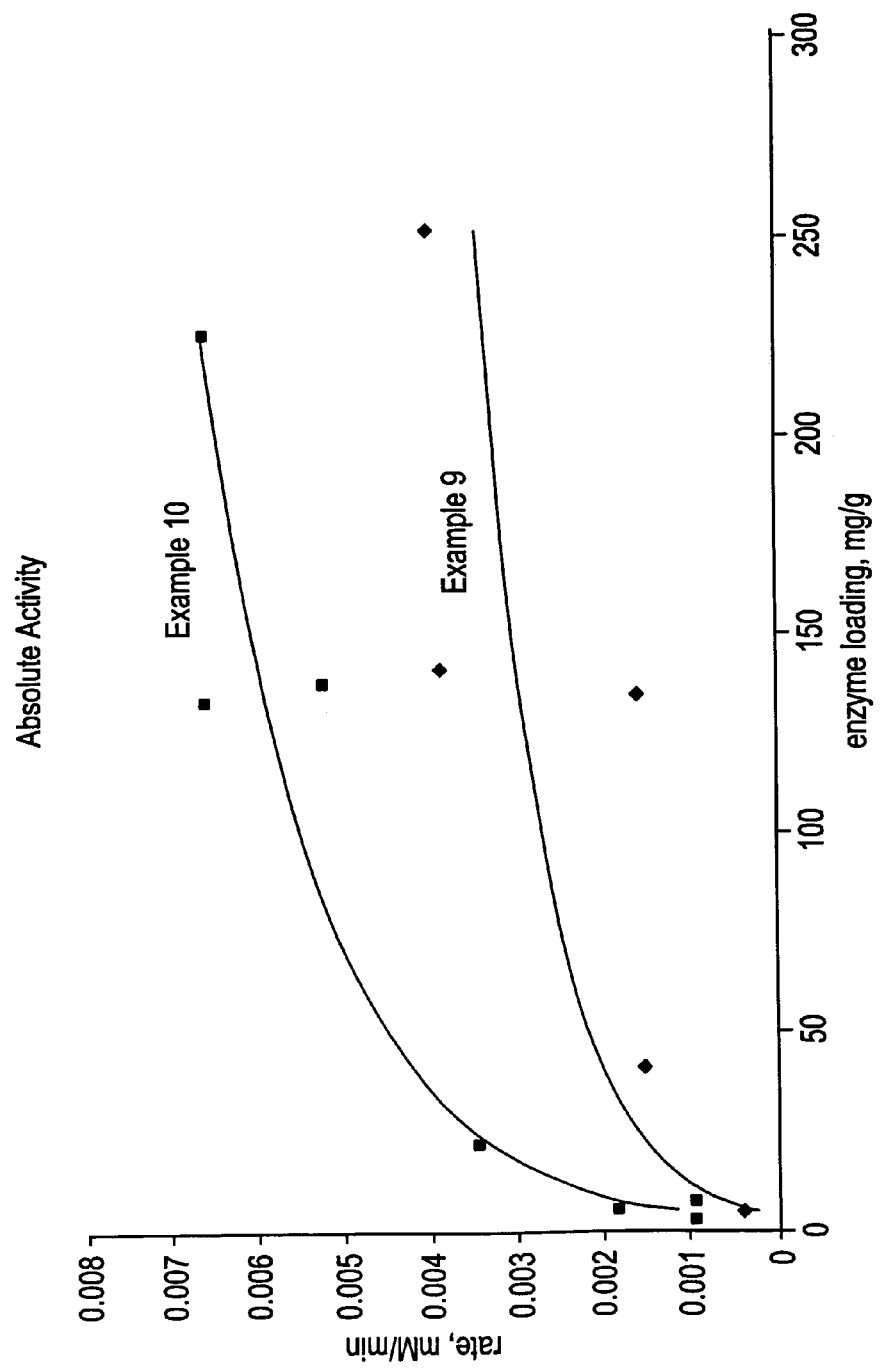
FIG. 11 shows the comparison of the absolute rate for the hydrolysis of tetrapeptide catalyzed by α-chymotrypsin (CT) when the enzyme loading is varied on the supports of Example 9 and Example 10.
Figure 12:
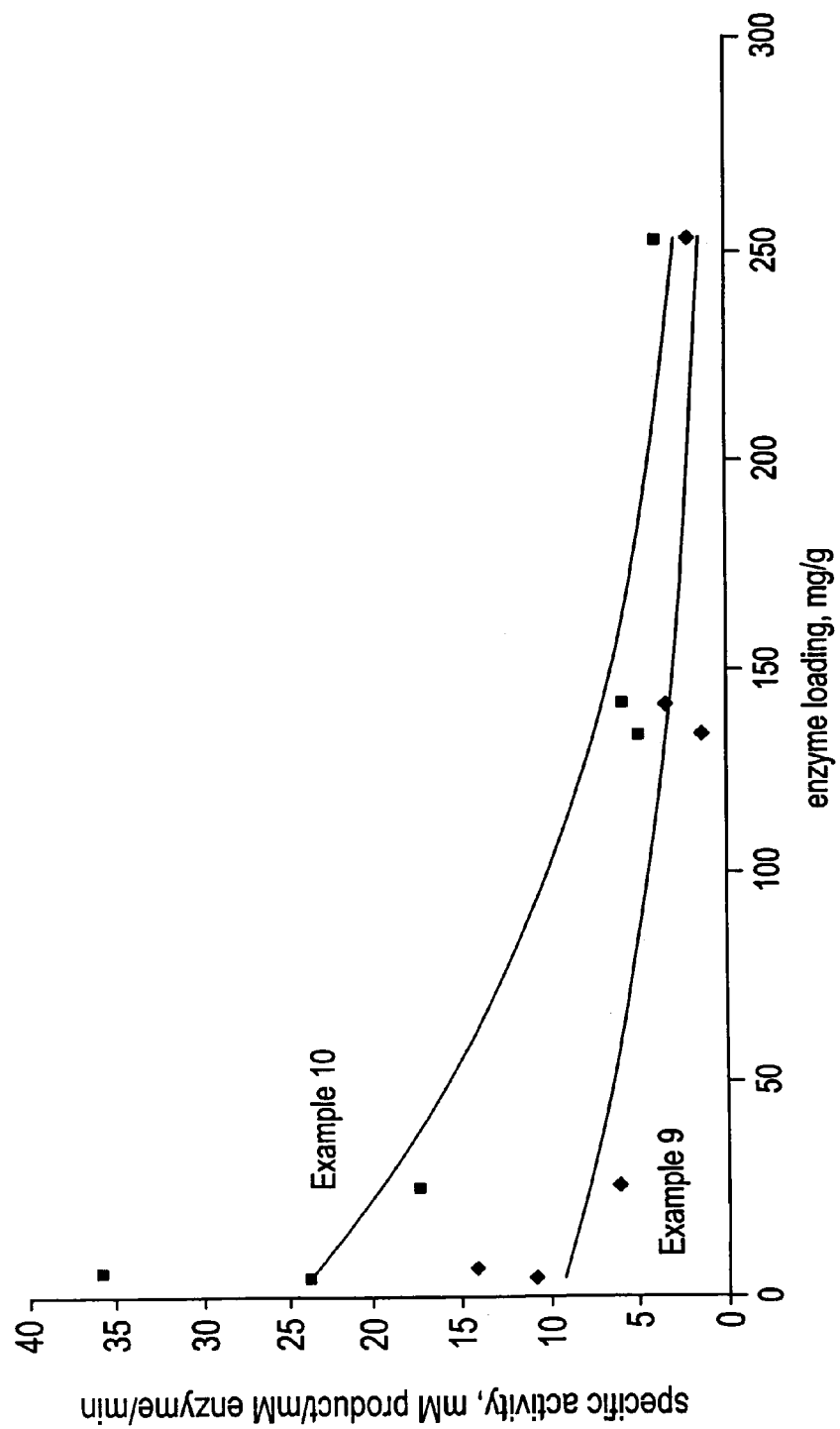
FIG. 12 shows the specific activity (per mM of enzyme) versus loading for the supports of Examples 9 and 10.

FIG. 11 shows the comparison of the absolute rate for the hydrolysis of tetrapeptide catalyzed by CT when the enzyme loading is varied on the support of Example 9 or Example 10. The results clearly show the large rate enhancement when the enzyme is supported on the support of Example 10, the passivated surface. Note also that as the loading increases, the absolute rate levels off indicating that there is an optimum loading for this enzyme and an optimum pore size distribution of the silica, as there should be. This is shown in FIG. 12 illustrating the specific activity (per mM of enzyme) versus loading for the supports of the two Examples. Again, the specific activity is much higher for the support of Example 10 than for the support of Example 9.

Example 13

Figure 13:
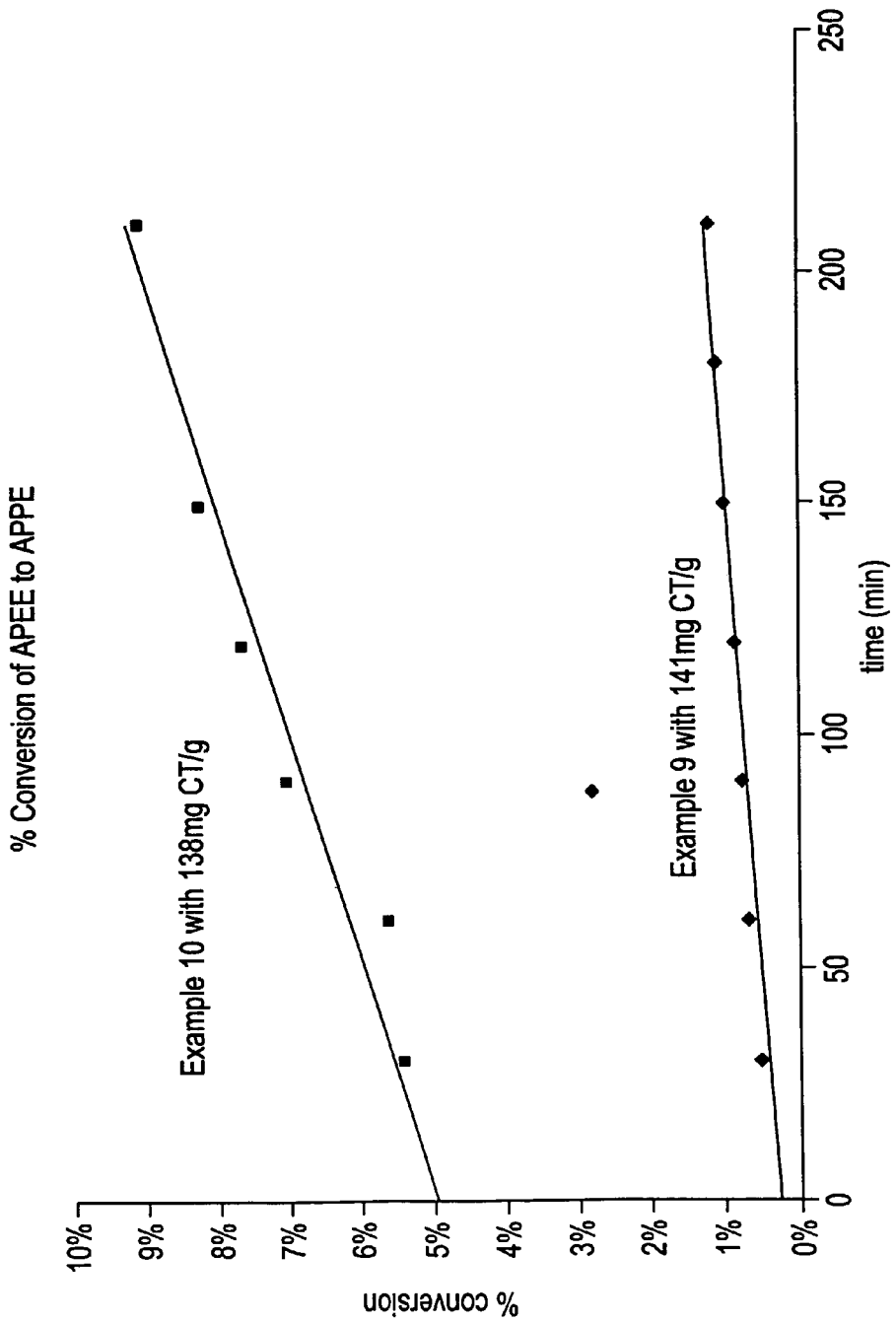
FIG. 13 shows the conversion versus time for α-chymotrypsin (CT) immobilized on the supports of Example 9 (141 mg CT/g) and Example 10 (138 mg CT/g).

Catalysis: α-Chymotrypsin Organic
Reaction—Transesterification of a Methyl Ester to a Propyl Ester An appropriate amount of immobilized CT was placed in a 20 ml glass scintillation vial (15 mg preparations are used for most reactions). 5 ml of a reaction mixture containing 1.0 M propanol and 25 mM n-acetyl-L-phenylalanine were added to the scintillation vial to initiate the reaction. The reaction was allowed to proceed in a 30° C. incubating shaker (200 rpm) at a 45° angle. Aliquots were withdrawn at appropriate time intervals during the period in which total conversion remained below 10%. This ensures that calculated initial rates are based on the linear reaction time period. The aliquots were spun down in 1.5 ml eppendorf centrifuge tubes to remove immobilized enzyme. The supernatant was then analyzed via GC. FIG. 13 shows the conversion versus time for when the CT is supported on the support of Example 9 (141 mg CT/g) or Example 10 (138 mg CT/g). Again, in this organic case, there is a large rate enhancement for the support of Example 10 over the support of Example 9 showing that the passivation of the surface prevents non-selective binding and gives a large activity advantage.

Example 14

Catalysis: B-Lipase Hydrolytic
Reaction—Hydrolysis of Tributyrin

In this hydrolysis, the substrate tributyrin was hydrolyzed by a *Candida anartica* B-lipase at the ester bond between the glycerol and the butyric acid. The butyric acid liberation was followed in the pH stat system by monitoring the amount of base added to the solution as the reaction progresses. As the reaction progressed, the acidification due to the liberation of butyric acid was followed and initial rates readily calculated. A calibration curve was made with pure butyric acid to convert base delivered to extent of reaction.

50 mg of the lipase supported on the support of Example 9 or 10 were added to 25 ml of 100 mM PBS+150 mM NaCl buffer (pH 7.0) in the pH stat reaction vessel. All experiments were carried out at a critical stirring speed, which overcomes the oil/water interface limitation to the reaction. The reaction was initiated by adding 730 µl of the tributyrin (final concentration of 0.1 M) to the reaction mixture. The reaction was allowed to progress for at least 10 minutes to get a linear rate of base uptake. (Ideally, all measurements are done before 10% of total conversion has occurred). Trial and error determined the time interval between readings, with total time courses ranging from as long as 40 minutes for low enzyme loading to as short as 10 minutes for the highest enzyme loading.

Figure 14:
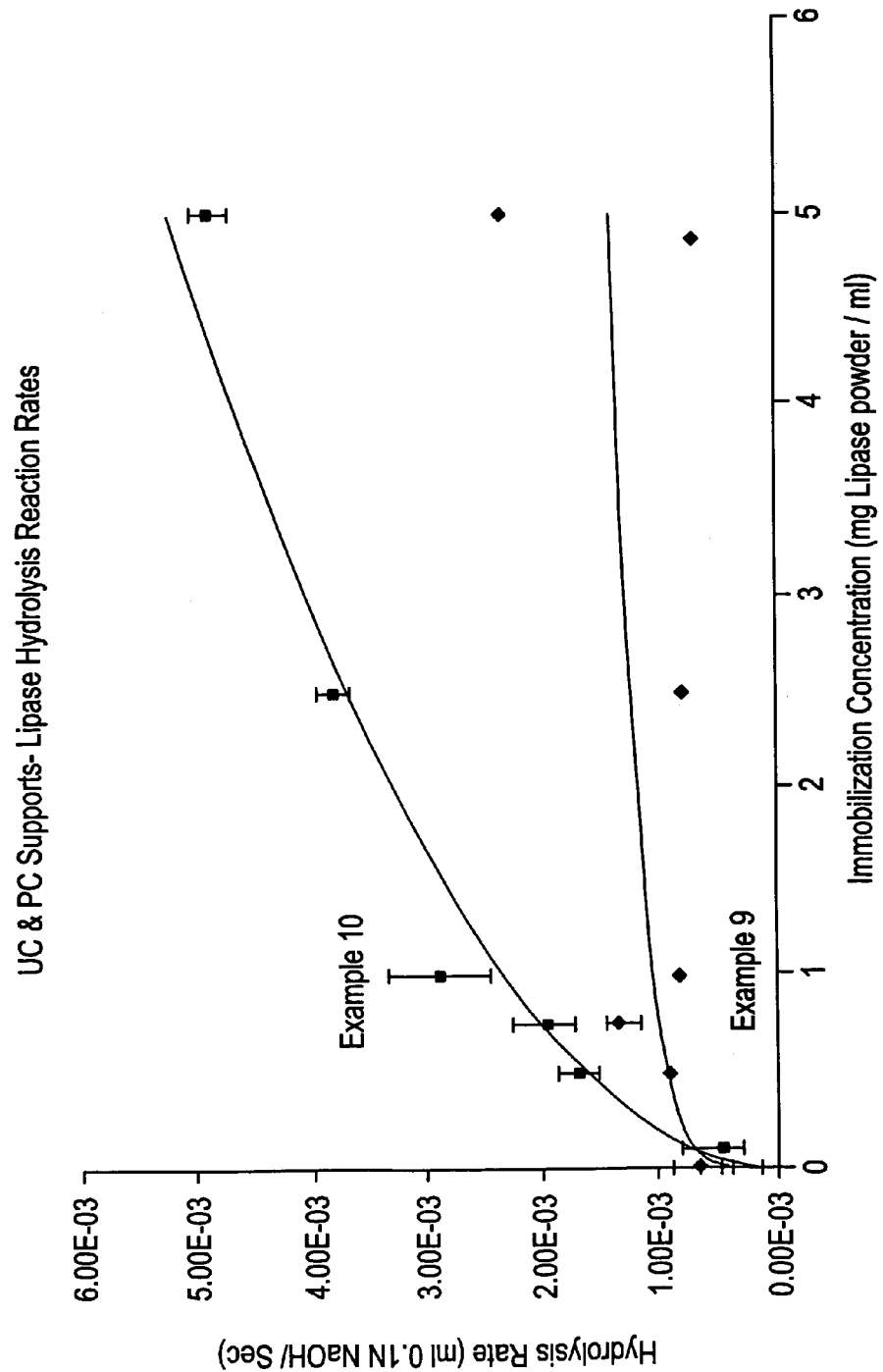
FIG. 14 shows the comparison of the absolute rate for the hydrolysis of tributyrin catalyzed by B-lipase when the enzyme loading is varied on the supports of Example 9 and Example 10.

FIG. 14 shows the comparison of the absolute rate for the hydrolysis of tributyrin catalyzed by B-lipase when the enzyme loading is varied on the support of Example 9 or Example 10. These results clearly show the large rate enhancement when the enzyme is supported on the support of Example 10, the passivated surface. Whereas, the activity is essentially gone when the enzyme is supported on the unpassivated surface of Example 9.

Example 15

Catalysis: B-Lipase Organic Reaction—Transesterification of Sec-Phenylethyl Alcohol In this trans-esterification, the substrate alcohol (sec-phenylethyl alcohol) was acylated with the acetate ester (vinyl acetate). As the reaction progressed, the peaks for the substrate and product were monitored via GC. A 100 mM stock solution of sec-phenylethyl alcohol in hexane spiked with 300 mM vinyl acetate was initially prepared.

10 mg of the lipase (Candida anartica) were added to a reaction vessel. To initiate the reaction, 5.0 ml of the stock solution was added by pipette to the reaction vessel (20 ml or larger vessel). The reaction was allowed to progress at room temperature in a shaker between time course measurements. As the reaction progressed, no change was apparent. To take a measurement, 0.25 ml of the reaction mixture (silica support included) were added by pipette to a 2.0 ml centrifuge tube and spun. The remainder of the reaction mixture was allowed to continue shaking. 0.150 ml of the supernatant from the centrifuge tube were removed by pipette, being careful not to disturb the silica at the bottom, and placed into a limited volume GC vial. (Ideally, all measurements are done before 10% of total conversion has occurred.) It takes some trial and error to determine the time interval between measurements. However, a minimum of 8 time points should be taken for each reaction to determine initial rates. Total time courses herein were taken over a period of 300 minutes.

Analysis of the reaction mixture was performed on a Shimadzu GC17A with an autosampler. The relevant method parameters are as follows:

| Column: | Supelco MDN-1 fused silica capillary column 30 m, 0.32 mm ID, 0.25 mm film thickness |
|---|---|
| Oven: | Isothermal at 125° C., wait time of 5.5 minutes, 250° C. injection port and detector temperatures |
| Injection: | 1.0 µl injection |
| Detector: | Flame Ionization |
| Elution: | Solvent - 2.6 minutes |
| | Substrate - 3.8 minutes |
| | Product - 5.0 minutes |

Figure 15:
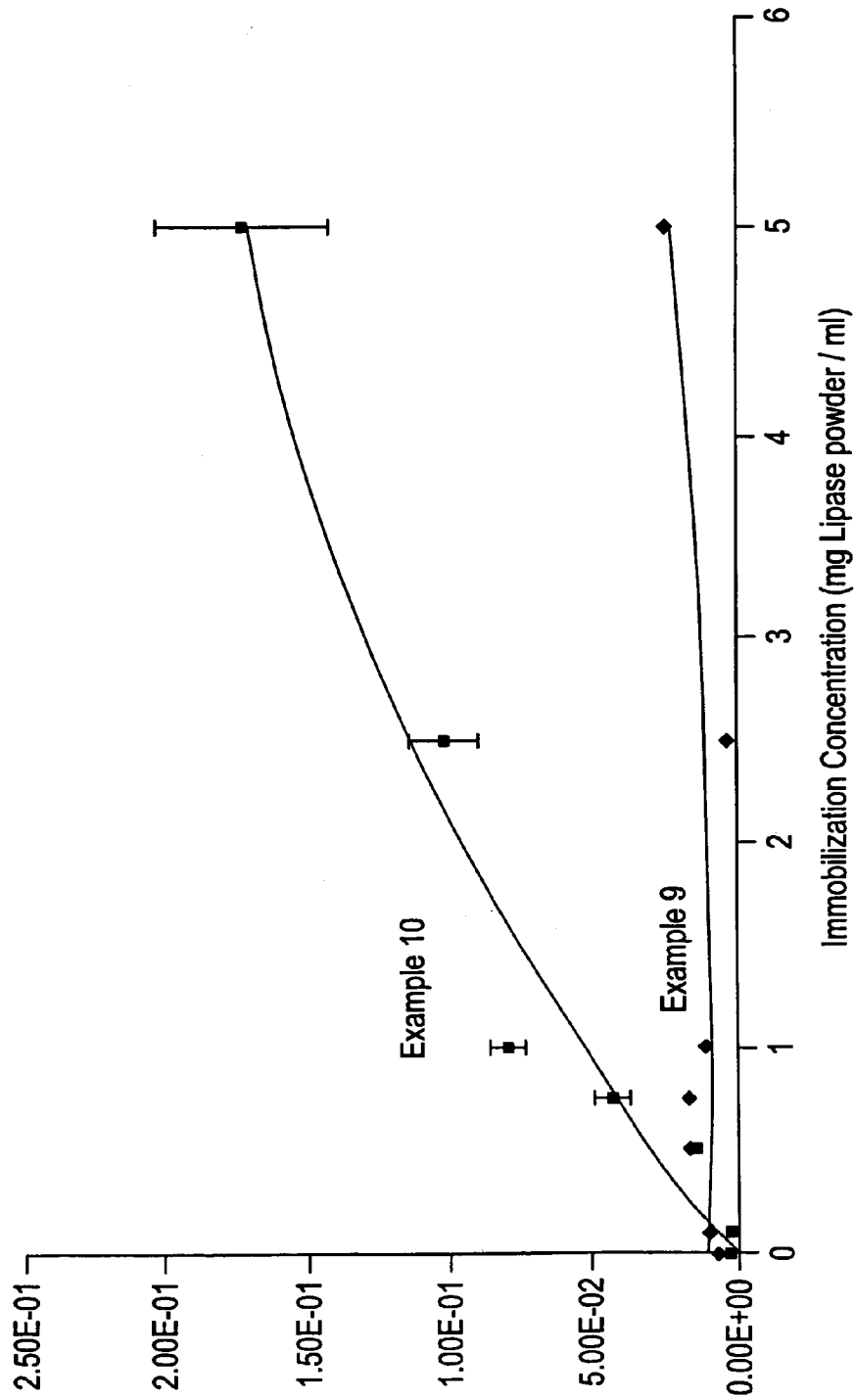
FIG. 15 shows the comparison of the absolute rate for the transesterification catalyzed by B-lipase when the enzyme loading is varied on the supports of Example 9 and Example 10.

FIG. 15 shows the comparison of the absolute rate for the transesterification catalyzed by B-lipase when the enzyme loading is varied on the support of Example 9 or Example 10. These results clearly show the large rate enhancement when the enzyme is supported on the support of Example 10, the passivated surface. Whereas the activity is essentially gone when the enzyme is supported on the unpassivated surface of the support of Example 9.

All articles, books, patents, patent applications and patent publications cited herein are incorporated by reference in their entirety. While the invention has been described in conjunction with examples and preferred embodiments, it is to be understood that the foregoing description is exemplary and explanatory in nature and is intended to illustrate the invention and its preferred embodiments. Through routine experimentation, one of ordinary skill in the art will recognize apparent modifications and variations that may be made without departing from the spirit of the invention. Thus, the invention is intended to be defined not by the above description, but by the following claims and their equivalents.

The invention claimed is:

1. A method for reducing non-specific binding to an inorganic support comprising a supported catalyst system, said support having at least one functional group capable of non-specific binding, the method comprising:
   (a) providing an inorganic support having at least one function group capable of reacting non-selectively with a catalytic species, a reaction substrate, reaction product, or other molecule;
   (b) reacting said at least one functional group of the inorganic support with a reactant capable of forming a $R_{10}$ group on the support to provide at least one $R_{10}$ group on at least one surface of the inorganic support, wherein the $R_{10}$ group comprises at least one non-acidic, hydrophilic, hydroxyl containing organic group;
   (c) reacting the inorganic support with at least one linker to provide at least one linker attached to at least one surface of the support; and
   (d) reacting the linker with a catalytic species to immobilize the catalytic species on the support, wherein the $R_{10}$ group is present on the surface of the inorganic support in a concentration sufficient to reduce and/or prevent non-specific binding.

2. The method of claim 1 wherein the $R_{10}$ group is selected from the group consisting of —$CH_2OH$, —$CH(OH)_2$, —$CH(OH)CH_3$, —$CH_2CH_2OH$, —$C(OH)_2CH_3$, —$CH_2CH(OH)_2$, —$CH(OH)CH_2(OH)$ and mixtures thereof.

3. The method of claim 2 wherein the $R_{10}$ group is selected from the group consisting of —$CH_2OH$, —$CH(OH)CH_3$, —$CH_2CH_2OH$ and mixtures thereof.

4. The method of claim 3, wherein the $R_{10}$ group is —$CH_2OH$.

5. The method of claim 1, comprising a concentration of $R_{10}$ groups ranging from about 1 to about 10 $R_{10}$ groups per $nm^2$ of inorganic support.

6. The method of claim 1, wherein the inorganic support is an inorganic metal oxide.

7. The method of claim 6 wherein the functional group capable of reacting with the catalytic species, a reaction substrate or reaction product is a hydroxyl group on the surface of the support.

8. The method of claim 7 wherein the $R_{10}$ groups are present on the support in a concentration sufficient to cover from about 50 to about 90% of the hydroxyl groups on the surface of the support.

9. The method of claim 8 wherein the $R_{10}$ groups are present on the support in a concentration sufficient to cover from about 75% to about 99% of the surface hydroxyl groups on the surface of the support.

10. The method of claim 1 wherein the $R_{10}$ groups are attached to the surface of the support through a bivalent moiety or atom reactant attached to the surface of the support.

11. The method of claim 1 wherein the $R_{10}$ groups are attached directly to the surface of the support.

12. The method of claim 6 wherein the inorganic metal oxide is a silicate or aluminosilicate.

13. The method of claim 6 wherein the inorganic metal oxide is selected from the group consisting of silica, alumina, silica-alumina, zirconia, zirconate, titania, controlled pore glass and mixtures thereof.

14. The method of claim 13 wherein the inorganic metal oxide is silica.

15. The method of claim 14 wherein the silica is chromatographic grade silica or a silica gel.

16. The method of claim 1, wherein the inorganic support is magnetically responsive.

17. The method of claim 1, wherein the linker is an optionally substituted bivalent chemical group.

18. The method of claim 1, comprising a concentration of linker of from about 0.1 to 5.0 linkers per $nm^2$ of support.

19. The method of claim 1, wherein the support comprises a concentration of a catalytic species sufficient to catalyze a desired reaction.

20. The method of claim 19, wherein the catalytic species is an enzyme.

21. The method of claim 20, wherein the support comprises from about 0.04 to about 4 enzymes per $nm^2$.

22. The method of claim 20 wherein the inorganic support is silica and the $R_{10}$ group is —$CH_2OH$.

23. The method of claim 22 wherein the silica is a silica gel or chromatographic grade silica.

24. The method of claim 19 wherein the catalytic species is an organometallic complex.

25. The method of claim 19 wherein the catalytic species is an organic molecule, fragment or complex.

* * * * *